United States Patent
Hutchinson et al.

(10) Patent No.: US 6,929,608 B1
(45) Date of Patent: *Aug. 16, 2005

(54) APPARATUS FOR DEPOSITION OF ULTRASOUND ENERGY IN BODY TISSUE

(75) Inventors: Erin Hutchinson, Boston, MA (US); Mark Buchanan, Burlington, MA (US); Kullervo Hynynen, Medfield, MA (US)

(73) Assignee: Brigham and Women's Hospital, Inc., Boston, MA (US)

( * ) Notice: Subject to any disclaimer, the term of this patent is extended or adjusted under 35 U.S.C. 154(b) by 470 days.

This patent is subject to a terminal disclaimer.

(21) Appl. No.: 09/692,294

(22) Filed: Oct. 19, 2000

Related U.S. Application Data

(63) Continuation of application No. 08/747,033, filed on Nov. 8, 1996, now Pat. No. 6,135,971.

(60) Provisional application No. 60/006,413, filed on Nov. 9, 1995.

(51) Int. Cl.[7] .............................................. A61B 8/00
(52) U.S. Cl. ..................... 600/439; 600/437; 600/447; 600/459; 601/2; 601/3; 601/4; 604/22
(58) Field of Search ......................... 604/22; 601/2–4; 600/439, 447, 459, 437

(56) References Cited

U.S. PATENT DOCUMENTS

| | | | |
|---|---|---|---|
| 4,052,723 A | 10/1977 | Miller | |
| 4,166,967 A | 9/1979 | Benes et al. | |
| 4,180,792 A * | 12/1979 | Lederman et al. | 342/380 |
| 4,242,912 A * | 1/1981 | Burckhardt et al. | 310/334 |
| 4,460,841 A * | 7/1984 | Smith et al. | 310/334 |
| 4,549,533 A | 10/1985 | Cain et al. | |
| 4,586,512 A | 5/1986 | Do-huu et al. | |
| 4,604,543 A * | 8/1986 | Umemura et al. | 310/334 |
| 4,646,756 A | 3/1987 | Watmough et al. | |
| 4,658,176 A * | 4/1987 | Nakaya et al. | 310/334 |
| 4,776,086 A | 10/1988 | Kasevich et al. | |
| 4,797,682 A | 1/1989 | Klimczak | |
| 4,860,752 A | 8/1989 | Turner | |
| 4,890,268 A | 12/1989 | Smith et al. | |
| 4,938,217 A | 7/1990 | Lele | |
| 4,960,107 A | 10/1990 | Aida et al. | |

(Continued)

FOREIGN PATENT DOCUMENTS

SU      1630854 A1      2/1991

OTHER PUBLICATIONS

Hutchinson, et al., "MRI Feedback Control for Phased Array Prostate Hyperthermia", 1996 IEEE Conference, pp. 1-4.

(Continued)

Primary Examiner—Brian L. Casler
Assistant Examiner—William Jung
(74) Attorney, Agent, or Firm—Mintz, Levin, Cohn, Ferris, Glovsky and Popeo, P.C.; Ivor R. Elrifi; Shane H. Hunter

(57) ABSTRACT

An apparatus for providing ultrasonic energy for deposition in body tissue including an array of elements having at least two different sizes and at least one element being aperiodically spaced with the respect to other elements in the array. Excitation of the elements produces a beam of ultrasonic energy having reduced grating lobes. Reduced grating lobe magnitude permits improved ultrasonic beam focusing and/ or the use of larger element sizes.

17 Claims, 18 Drawing Sheets

U.S. PATENT DOCUMENTS

| | | | |
|---|---|---|---|
| 5,091,893 A | 2/1992 | Smith et al. | |
| 5,097,844 A | 3/1992 | Turner | |
| 5,158,071 A * | 10/1992 | Umemura et al. | 600/439 |
| 5,167,231 A * | 12/1992 | Matsui | 310/336 |
| 5,186,181 A | 2/1993 | Franconi et al. | |
| 5,233,673 A | 8/1993 | Vali et al. | |
| 5,251,645 A | 10/1993 | Fenn | |
| 5,295,484 A | 3/1994 | Marcus et al. | |
| 5,307,812 A | 5/1994 | Hardy et al. | |
| 5,323,779 A | 6/1994 | Hardy et al. | |
| 5,327,884 A | 7/1994 | Hardy et al. | |
| 5,327,895 A | 7/1994 | Hashimoto et al. | |
| 5,343,211 A | 8/1994 | Kott | |
| 5,385,544 A | 1/1995 | Edwards et al. | |
| 5,391,197 A | 2/1995 | Burdette et al. | |
| 5,441,532 A | 8/1995 | Fenn | |
| 5,465,725 A * | 11/1995 | Seyed-Bolorforosh | 310/366 |
| 5,651,365 A * | 7/1997 | Hanafy et al. | 29/25.35 |
| 5,706,820 A * | 1/1998 | Hossack et al. | 29/25.35 |
| 6,135,971 A * | 10/2000 | Hutchinson et al. | 601/3 |
| 6,168,564 B1 * | 1/2001 | Teo | 600/443 |

OTHER PUBLICATIONS

Granz, "*Measurement of Shock Wave Properties after the Passage through a Tissue mimicking material*", 1994 Ultrasonics Symposium, pp. 1847-1851.

Umemura, et al., "*Reduction of Threshold for Producing Sonodymaic Tissue Damage by Second-Harmonic Superimposition*", 1995 IEEE Ultrasonics Symposium, pp. 1567-1570.

Spoo, et al., "*Activation of photodynamic substances by high-energy-ultrasoound-a new tharapeutic principle?*", 1994 Ultrasonics Symposium, pp. 1857-1860.

Steinberg, "*The Peak Sidelobe of the Phased Array Having Randomly Located Elements*", IEEE Transactions on Antennas and Propagation, vol. AP-20, No. 2, Mar. 1972, pp. 129-136.

Hutchinson, et al., "*Evaluation of an Aperiodic Phased Array for Prostate Thermal Therapies*", 1995 IEEE Ultrasonics Symposium, pp. 1601-1604.

* cited by examiner

FIG. 1(b)
*(PRIOR ART)*
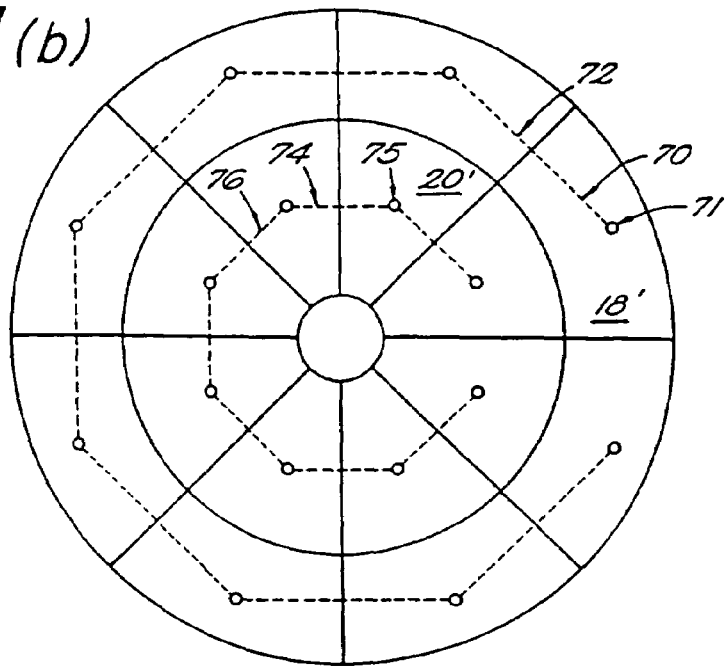
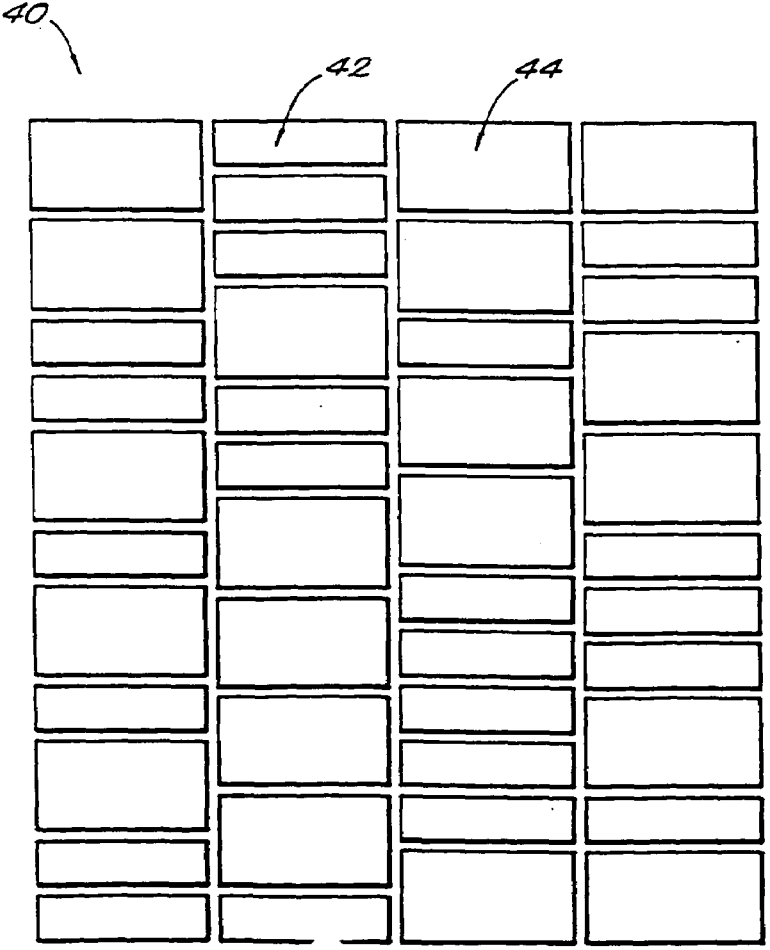
FIG. 2

APPARATUS FOR DEPOSITION OF ULTRASOUND ENERGY IN BODY TISSUE

This application is a continuation of 08/747,033 (filed Nov. 8, 1996), which became U.S. Pat. No. 6,135,971 which claims benefit of 60/006,413 filed Nov. 9, 1995 and titled "Aperiodic Ultrasound Phased Array".

STATEMENT AS TO FEDERALLY SPONSORED RESEARCH

This invention was made with U.S. Government support under National Institutes of Health grant No. R01CA48939. The government has certain rights in the invention.

TECHNICAL FIELD

The present invention relates to medical devices generally and, more particularly, to devices for ultrasound deposition in body tissue for use in medical treatment.

BACKGROUND OF THE INVENTION

The deposition of ultrasonic energy within the human body has numerous useful and promising medical applications. For example, ultrasound may be used for tissue ablation, diagnostic imaging, drug delivery, and other therapies which employ heat, cavitation, shock waves (e.g. destroying kidney stones) or other thermal and/or mechanical effects for therapeutic purposes.

A particularly advantageous use for ultrasonic energy deposition is thermal therapy (also known as hyperthermia, tissue ablation, and/or thermal surgery) which treats internal cancers and other internal diseases that respond to increases in body tissue temperature. Thermal therapy entails generating an ultrasonic energy beam and electrically focusing and controlling the energy beam to provide localized energy deposition in body tissue thereby heating the body tissue. Clearly, it is critical that the ultrasonic energy be focused to treat a desired target area of body tissue, and to avoid applying ultrasonic energy outside of the target area.

Prior art ultrasonic energy applicators typically have focusing and power difficulties. On the one hand, it is desirable to use high-frequency ultrasound to focus the beam more sharply and to improve power absorption in the target tissue thereby reducing near field and post-focus heating. On the other hand, higher frequencies generally result in large "grating lobes" (i.e. secondary focal points around the target area) that result in undesired heating, cavitation or other thermal/mechanical effects in non-targeted tissues.

The conventional technique for reducing grating lobes is to use small radiating elements having a center-to-center spacing of half a wavelength (or less) apart. However, small radiating elements have lower power capabilities, are less efficient, and are more costly to fabricate. Moreover, ultrasonic energy applicators that employ smaller elements are more difficult and expensive to produce since they require not only more radiating elements, but also additional power and control circuitry such as amplifier channels, phase shifters and wiring.

Therefore, it is an object of the present invention to provide an apparatus for ultrasonic energy deposition in body tissue with improved focusing capability.

It is another object of the present invention to provide an apparatus for ultrasonic energy deposition that reduces grating lobe magnitude.

It is still another object of the present invention to provide an apparatus for ultrasonic energy deposition that provides greater power, thereby reducing the time required to deposit a certain quantity of ultrasonic energy.

It is yet another object of the present invention to provide an apparatus for ultrasonic energy deposition that reduces the required number of radiating elements for a given grating lobe magnitude.

It is a further object of the present invention to provide a more efficient and cost-effective apparatus for ultrasonic energy deposition.

It is still a further object of the invention to provide an improved apparatus for ulrasonic energy deposition that can be used for tissue ablation, diagnostic imaging, drug delivery, and other therapies which employ heat, cavitation, shock waves or other thermal and/or mechanical effects for therapeutic purposes.

SUMMARY OF THE INVENTION

The foregoing objects are attained by the present invention which provides an apparatus for ultrasonic energy deposition in body tissue which includes an array of radiating elements of at least two different sizes (i.e., some elements are of one size, others are of another size, and so forth), at least one element of which is aperiodically spaced with respect to the other elements. Thus, for example, an array can include a plurality of elements, most of which are regularly spaced with respect to one another, and at least one (and, preferably more) of which is aperiodically spaced with respect to the others. The array is used to generate a beam of ultrasound energy by exciting its component radiating elements.

The aperiodic spacing of at least one of the elements reduces the overall periodicity of the array which, in turn, reduces grating lobe accumulation in the beam. The beam produced by the array can be focused more tightly, resulting in reduced risk of undesired thermal/mechanical impact on non-targeted areas. Furthermore, aperiodic spacing does not diminish the density of the array, the power per unit area of the array, or materially reduce the array efficiency. Reduced grating lobes also permits the use of larger element widths. With larger elements, fewer total elements are necessary to produce a certain measure of localized energy deposition.

Another aspect of the invention provides an apparatus for ultrasonic energy deposition including an excitation mechanism coupled to the elements of an array as described above for providing electrical excitations to those elements. The apparatus can also include a phase shifting mechanism coupled to the excitation mechanism to provide the elements with electrical excitations of differing and/or adjustable phases. This permits the apparatus to controllably apply the beam over a region of body tissue. For example, the phase shifting mechanism can be employed to dynamically "scan" the beam over a region of body tissue, thereby facilitating ablation, therapy, or imaging of large volumes of tissue. Moreover, the phase shifting mechanism can be used to control the area or volume of the region, to control the amount of energy applied to the region, or to control the period of time over which the beam is applied to the region or portions thereof. By providing such control, the phase shifting mechanism facilitates optimization of ultrasonic dose profiles (and, therefore, temperature, cavitation, etc.).

An additional aspect of the invention provides an apparatus for ultrasonic energy deposition wherein the array as described above includes an arrangement of elements in a linear-plane or, in two dimensions or three dimensions.

Thus, for example, the array can be comprised of a single, flat row of elements whereby the elements are in a linear-plane arrangement. In another example, the array includes multiple rows of elements in a two dimensional arrangement or, the array can be comprised of elements on a surface of a section of sphere to give the elements of the array a three dimensional arrangement.

Furthermore, the arrangement of elements, whether in a linear-plane or in two or three dimensions, can be optimized by using a method of optimized random distribution. That method can include steps of deriving a cost function and calculating the value of the cost function for a plurality of random element sizes and positions. An optimal arrangement of elements can be chosen based upon the calculated value of the cost function. Preferably, the cost function includes a quotient of a maximum focusing power and a maximum corresponding grating lobe power.

A further aspect of the invention provides an apparatus for ultrasonic energy deposition including spacers located between elements of the array described above. The spacers dictate the spacing between edges of adjacent elements. Thus, if the spacers are uniformly sized throughout the array, the edges of the elements will be uniformly spaced from adjacent element edges. However, in accordance with this invention, the spacers can also be of different sizes such that the element edges are not uniformly spaced from adjacent element edges. Different sized spacers may enhance the aperiodic nature of the array and further reduce grating lobe magnitude.

BRIEF DESCRIPTION OF THE DRAWINGS

A more complete understanding of the invention may be attained by reference to the drawings, in which:

FIG. 1($a$) is a schematic top view of the embodiment of FIG. 1 according to the present invention.

FIG. 1($b$) is a prior art schematic top view of a two-dimensional planer arrangement of radiating elements.

FIG. 2($a$) is a schematic top view of another embodiment of a two-dimensional planer arrangement of radiating elements according to the present invention.

FIG. 5($b$) is a graphical representation of dose simulations of a single stationary focus, a uniform power scan, a scan optimized for uniform temperature, and a scan optimized for uniform dose using the deterministic method of optimizing focus weighing factors of FIG. 4.

FIG. 5($c$) is a graphical representation of dose simulations of a single stationary focus, a uniform power scan, a scan optimized for uniform temperature, and a scan optimized for uniform dose using the deterministic method of optimizing focus weighing factors of FIG. 4.

FIG. 13($b$) shows simulated results for the array conditions of FIG. 13($a$).

FIG. 14($b$) shows simulated results for the array conditions of FIG. 14($a$).

FIG. 15($b$) shows simulated results for the array conditions of FIG. 15($a$).

FIG. 16($b$) shows simulated results for the array conditions of FIG. 16($a$).

FIG. 17($b$) is a graph showing isothermal dose lines, as in FIG. 17($a$), for a plane parallel to the array surface and 3.5 cm deep.

FIG. 18($b$) is a graph showing simulated necrosed tissue lesions in a plane parallel to the array surface and 4 cm deep.

DETAILED DESCRIPTION OF THE PREFERRED EMBODIMENTS

Figure 1:
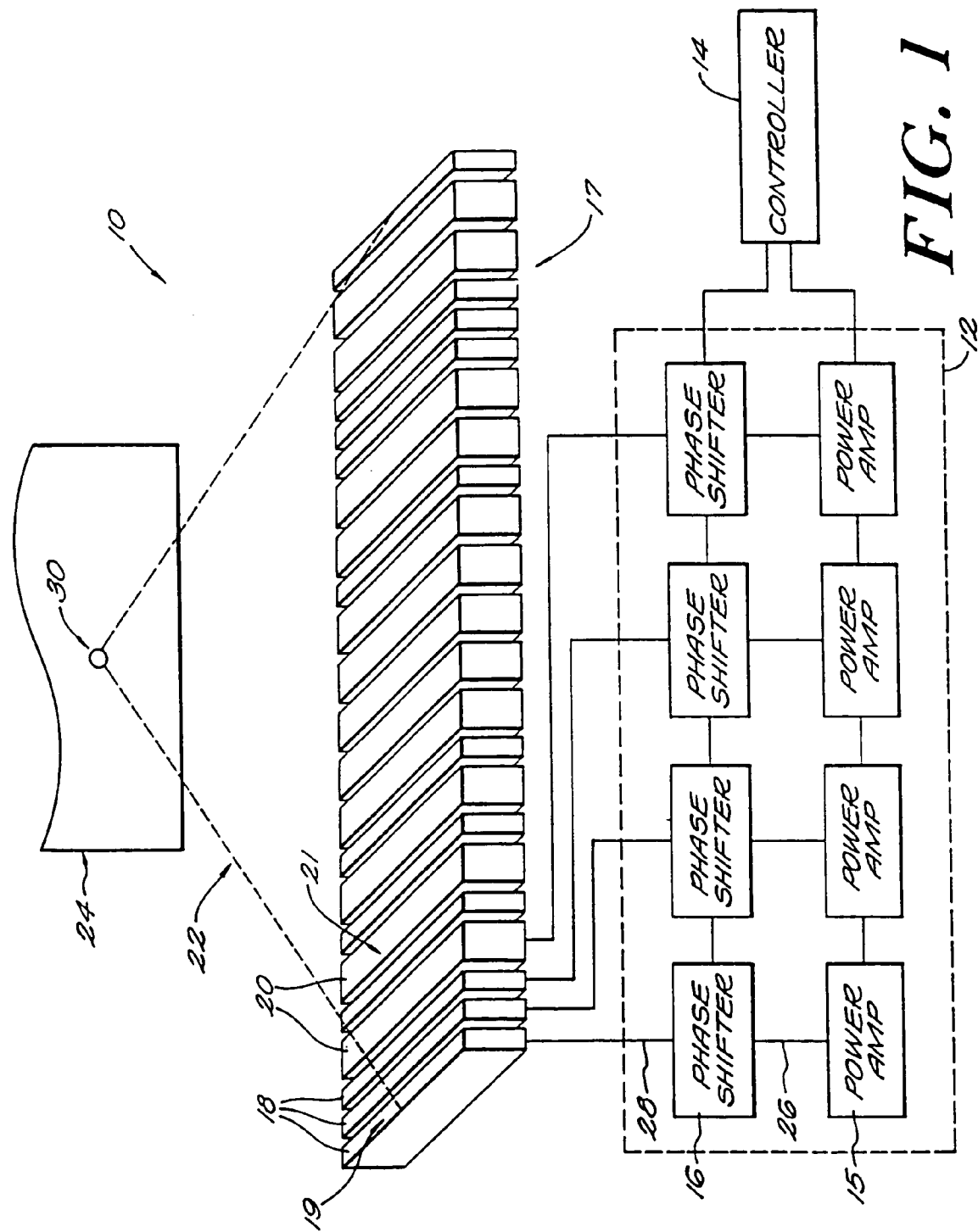
FIG. 1 is a schematic view of a linear planer embodiment according to the present invention.

Shown in FIG. 1 and designated generally by reference numeral 10 is an apparatus for deposition of ultrasonic energy according to the present invention. The ultrasonic energy apparatus 10 includes an amplifier system 12, a controller 14 and an array 17. When powered (and controlled) by amplifier 12, array 17 generates an ultrasonic beam 22 with reduced grating lobes for deposition in body tissue 24. As used herein, "body tissue" refers to fluids, tissues or other structures on or within a patient's body.

Illustrated array 17 includes radiating elements 18, 20 of two different sizes. Thus, as seen in FIG. 1, elements labelled 18 have a smaller cross-section (and radiating capacity) than elements labelled 20. It will be appreciated that an array according to the invention can include elements of two, three, or more different sizes.

The amplifier system 12 includes amplifiers 15 and phase shifters 16. Each amplifier 15 is individually controllable and each generates an excitation signal 26 corresponding to an individual radiating element 18, 20. The amplifier system 12 utilizes conventional circuitry to provide signals 26 which excite corresponding elements 18, 20 to radiate ultrasonically. A typical amplifier system 12 compatible for use with the ultrasonic energy apparatus 10 of the present invention is commercially available from Advanced Surgical System (model UDS 6420).

The controller 14 can be either a standard or special-purpose computer programmed in accord with the teachings herein to control amplifier system 12 in a conventional manner and as further described herein to generate excitation signals 26 of desired frequency, amplitude and phase. As more fully described below, the controller 14 can also control and vary the amplitude of individual excitation signals 26 to apply ultrasound energy over a wide region with varied intensity of distribution. Those skilled in the art will appreciate that the controller 14 need not be a separate unit as depicted in FIG. 1, but may be integral with the amplifier system 12.

In a preferred embodiment, each phase shifter 16 is coupled to and controls a corresponding radiating element 18, 20. To this end, the phase shifters 16 adjust the phase of the excitation signals 26 generated by the power amplifier 15 and transmit a phase-shifted signal 28 to the radiating elements 18, 20. The phase shifters 16 utilize conventional circuitry to adjust the phase of the excitation signals 26 in accord with commands from controller 14. Together, the radiating elements 18, 20 "convert" the phase-shifted excitation signals 28 into beam 22.

The controller 14 controls the amplifier system 12 and the phase shifters 16 in a conventional manner to focus the beam 22 at a focal position 30 located in the body tissue 24. The controller 14 can also control the phase shifters 16 to phase-shift steer the beam 22 to move the location of focal position 30 within the body tissue 24. The focal position 30 can be moved both radially (in a direction perpendicular to the plane of the array 17) and/or axially (in a plane parallel to the plane of the array 17). Thus, the phase-shift steering of the focal position 30 can be used to selectively provide ultrasonic energy to a discrete portion of the body tissue 24. As compared to non-steered stationary arrays, phase-shift steering of the beam 22 can be used to rapidly electronically scan the focal position 30, across the body tissue, to increase the volume of treated body tissue by more than a factor of 300. This eliminates the need for mechanical positioning systems or multiple arrays with varying focal depths. Furthermore, various scanning techniques can provide an improved and more even distribution of ultrasonic energy to the desired discrete portion of the body tissue 17. By rapidly electronically scanning the focal position 30 across a desired area of the body tissue 17, the ultrasonic energy can be spread evenly and precisely. Another of these scanning techniques, apodization, individually controls the power level emitted by each radiating elements 18, 20. Yet another technique, probably best used for sharp steering angles, selectively reduces or eliminates the power emitted by certain radiating elements to appreciably reduce grating lobe levels in the array 17.

The radiating elements in array 17 are comprised of conventional ultrasonic radiation-generating materials and preferably are made of piezoelectric materials such as PZT-EC69 (available from EDO, Salt Lake City, Utah). The elements can be mounted in a frame (not shown) in a conventional manner (e.g. using a resilient bonding material such as silicone rubber) to form arrays of the types described herein. The elements can be of any conventional geometry, though, in the illustrated embodiment they are shown as parallelepipeds. The radiating elements are of at least two different sizes. Thus, for example, elements 18 are narrower than elements 20. Though FIG. 1 is not necessarily drawn to scale, the volume of a narrower element 18 is preferably at least 5% less than the volume of a wider element 20. Moreover, the area of a radiating surface 19 of a narrower element 18 is preferably at least 5% less, and still more preferably approximately 28% less, than the area of a radiating surface 21 of a wider element 20 (see also FIG. 7). When applying ultrasound to human body tissue using conventional amplification apparatus 12, the length and/or width of individual elements 18, 20 can be as large as several times the wavelength ($\lambda$) of the beam 22, or as small as $\lambda/2$ of the beam 22.

Linear array theory provides that element widths (center-to-center spacing) less than $\lambda/2$ should be used in order to avoid grating lobes for focusing on any steering angle, but for central axis focusing element widths (center-to-center spacing) of $\lambda$ can be used. The small element widths associated with high frequencies have numerous disadvantages which include making array construction difficult and requiring more elements, amplifier channels and wiring for a given array length. Another disadvantage of small element widths is that array efficiency tends to decrease as element width decreases. To complicate matters regarding element width selection, an appropriate width-to-thickness ratio must be chosen to avoid reduced element efficiency in the thickness vibration mode due to increases in other modes of vibration. In array design, a balance between acoustical power output, grating lobes and element width must be achieved for successful phased array operation.

It is desirable to provide relatively high power output and relatively large element widths together with relatively small grating lobes for use with ultrasound deposition. Grating lobe suppression techniques were first developed in the separately distinct field of radar phased arrays using methods such as wide band signals and thinned arrays with uniform element size and random element center spacing or spatial tapering. These techniques are ineffective for treating body tissue because medical ultrasound devices require high acoustical power output, while thinned array designs have a low packing density and produce unacceptably low power.

Another technique developed to reduce grating lobes was the derivation of formulas used to calculate the peak grating lobe level for arrays of randomly located isotropic and nonisotropic elements while varying the number of elements, the wavelength, array length, beam steering angle, and signal bandwidth. Again, as with thinned arrays, this technique uses uniform element sizes.

We have discovered that aperiodically spaced, different sized elements, such as elements 18, 20 in array 17, decreases the periodicity of grating lobes generated by each of the elements. As seen in FIG. 1, the narrower elements 18 are dispersed irregularly amongst similarly irregularly dispersed wider elements 20. This aperiodic spacing of different sized elements 18, 20 prevents grating lobes produced by individual elements from accumulating in identical locations.

Reduced periodicity of grating lobes generated by individual elements produces a net result of reduced grating lobes for the entire array 17. Grating lobe reduction has two useful applications: (1) reduction of peak grating lobe levels while maintaining a consistent average element width; and/or (2) maintaining a constant grating lobe level while increasing the average and minimum element width. Larger element widths are desirable because they more efficiently transmit energy per unit surface area. Other inherent advantages of larger elements is that they are easier to produce and fewer elements are needed to transmit a certain level of energy thereby reducing the necessary amplifier channels, phase shifters and wiring. As more completely detailed in a specific example below, in an aperiodic distribution of unequally sized elements according to the present invention, a 30–45% reduction in the grating lobe levels can be achieved, as compared to an array of uniformly sized elements with the same average element width. Alternatively, the average element width in this specific example could be increased by approximately 20–35% ($\approx\lambda/4.4$) while maintaining a constant grating lobe level.

As used herein, aperiodically spaced means that the spacing measured from center of mass-to-center of mass between two adjacent elements is not the same for all elements. Thus, an aperiodically spaced element is not part of a clear pattern formed by the other elements. As seen in FIG. 1, if measured from center of mass-to-center of mass, every adjacent element 18, 20 is not equally spaced from other adjacent elements 18, 20.

Figure 1A:
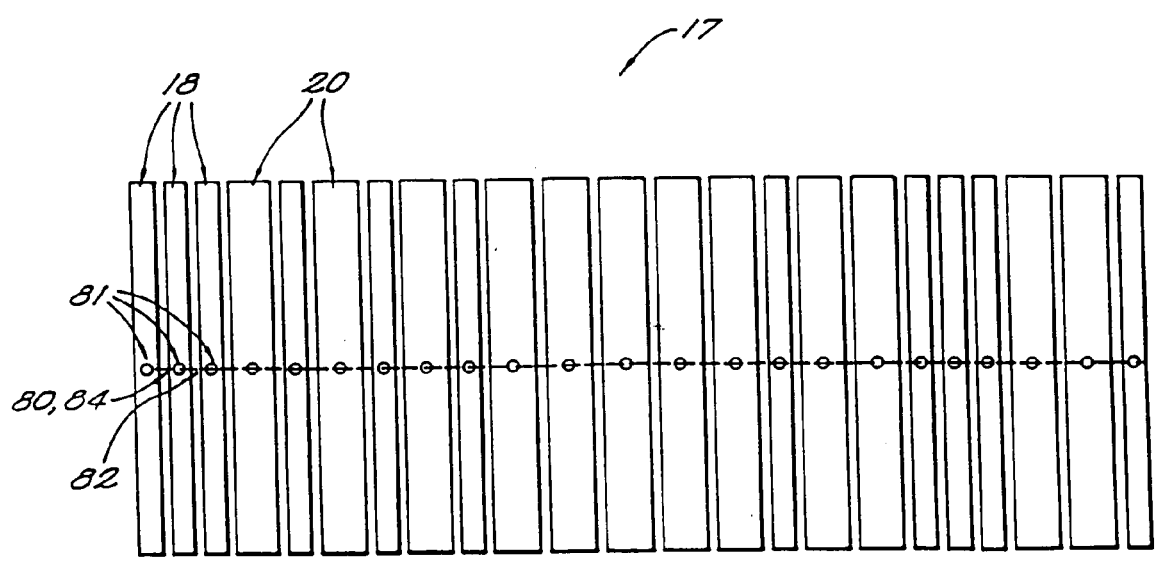

A characteristic of aperiodic spacing is depicted by drawing the shortest line possible which connects the centers of mass of the array elements. If the length of each adjacent center of mass-to-center of mass segment is not the same for the elements, then at least one of these elements is aperiodically spaced. Thus, it is readily apparent that none of the same-sized elements in FIG. 1(b) (prior art) are aperiodically spaced. Any shortest line 70 connecting the centers of mass 71 of same-sized elements 18' has seven adjacent segments 72 (each segment having endpoints defined by centers 71). Each segment 72, no matter how the shortest line 70 is drawn, has the same length and therefore none of the elements 18' are aperiodically spaced. Similarly, elements 20' are not aperiodically spaced because shortest line 74 joining element centers 75 also has identically sized adjacent segments 76. On the other hand, turning to FIG. 1(a) which is a top view of FIG. 1, one can readily see that the shortest line drawn 80 connecting the centers 81 of elements 18 would not have identically sized adjacent segments 82. Therefore, at least one of the elements 18 of FIG. 1(a) is aperiodically spaced. Likewise, the elements 20 of FIG. 1(a) have more than one differently sized segment 86 connecting adjacent same-sized element centers 85 via shortest line 84. Thus, at least one of the elements 20 is also aperiodically spaced.

Any number of elements 18, 20 may be aperiodically spaced. It is preferable that at least 10% of the elements are aperiodically spaced and, still more preferable that about 10–50% are so spaced. Of course, the invention also embraces arrays in which most or all elements are aperiodically spaced.

In FIG. 1, the elements 18, 20 are oriented side-by-side in a linear planar orientation. Spacers (not shown) are interposed between adjacent elements 18, 20 such that adjacent element edges to not touch. FIG. 1 depicts an array with spacers that are uniformly sized, but in order to increase the aperiodic geometry of the array 17, the spacers can be non-uniformly sized. With either uniform or non-uniform spacer sizing, the spacers should be smaller than the element 18, 20 size. The spacers can be made from a conventional silicone rubber material.

Figure 2:
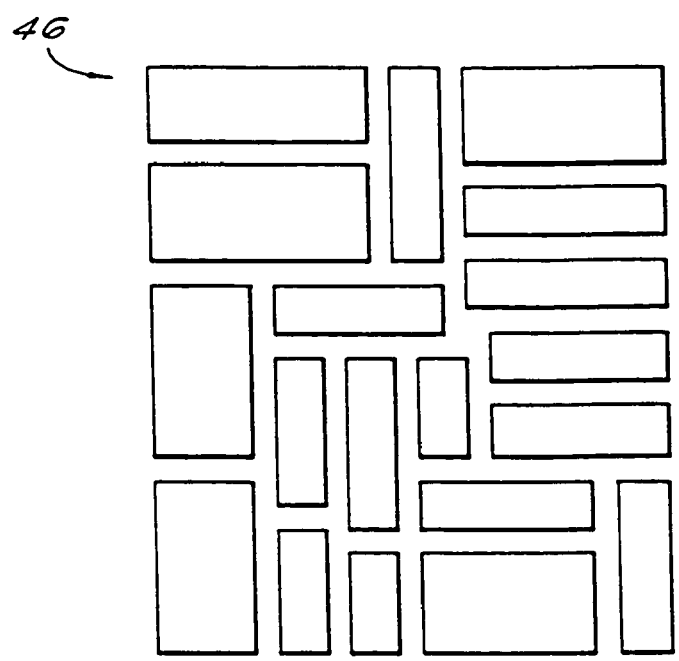
FIG. 2 is a schematic top view of a two-dimensional planer arrangement of radiating elements according to the present invention.
Figure 3:
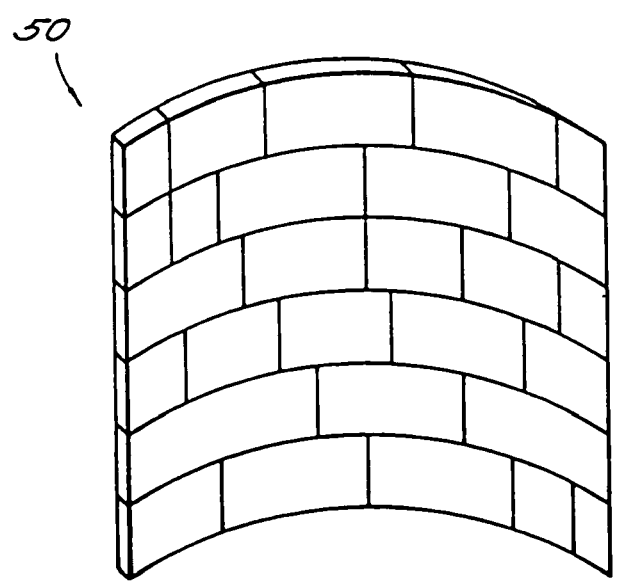
FIG. 3 is a schematic view of a three-dimensional arrangement of radiating elements according to the present invention.

It should be readily apparent that the aperiodic arrangement and geometry of the linear planer array 17 shown in FIG. 1 can be used in an infinite number of array geometries to produce similar advantages. For example, the array of FIG. 1 could be expanded in another dimension to form a two-dimensional array 40 as shown in FIG. 2. In FIG. 2, two differently sized elements 42, 44 are arranged to form a two-dimensional array 40 with aperiodically spaced elements. As shown in FIG. 2(a), the elements 46 can have more than two different sizes and need not be arranged in rows or columns. Similarly, FIG. 3 shows a non-planar three-dimensional cylindrical section array 50 having differently sized radiating elements arranged in a aperiodic fashion. Those skilled in the art will recognize that other two-dimensional geometries and other three-dimensional geometries, for example a spherical or sector-vortex shape, may also be utilized to arrange different sized elements aperiodically. Also, it is important to note that the elements shown in FIGS. 1, 2 and/or 3 need not have equal lengths or sizes or be arranged in rows to be in accordance with the present invention. Furthermore, it should be understood that the number of differently sized elements can be greater than two. Although it is preferable that no more than about 50% of the elements have the same size, for reasons of manufacturablity and arrangement optimization simplicity, it may be desirable to use only two different element sizes. However, any number of different element sizes may be used and may indeed further improve grating lobe reduction. Additionally, the element 18, 20 shape need not be rectangular as shown in FIG. 1, as other shapes arranged in an aperiodic fashion may also perform adequately.

To optimize the aperiodic arrangement of elements 18, 20 it is preferable that an arrangement optimization algorithm be used. The goal of the arrangement optimization algorithm is to select distributions of the different element widths which provide acceptable field patterns for a range of focal positions. The algorithm minimizes a cost function which is preferably designed to reduce grating lobe magnitude. An initial cost function is calculated from the initial array values. Such a cost function is presented in more detail below. The remainder of the arrangement algorithm iteratively minimizes the cost function to determine an optimized aperiodic arrangement of different sized elements 18, 20.

Figure 4:
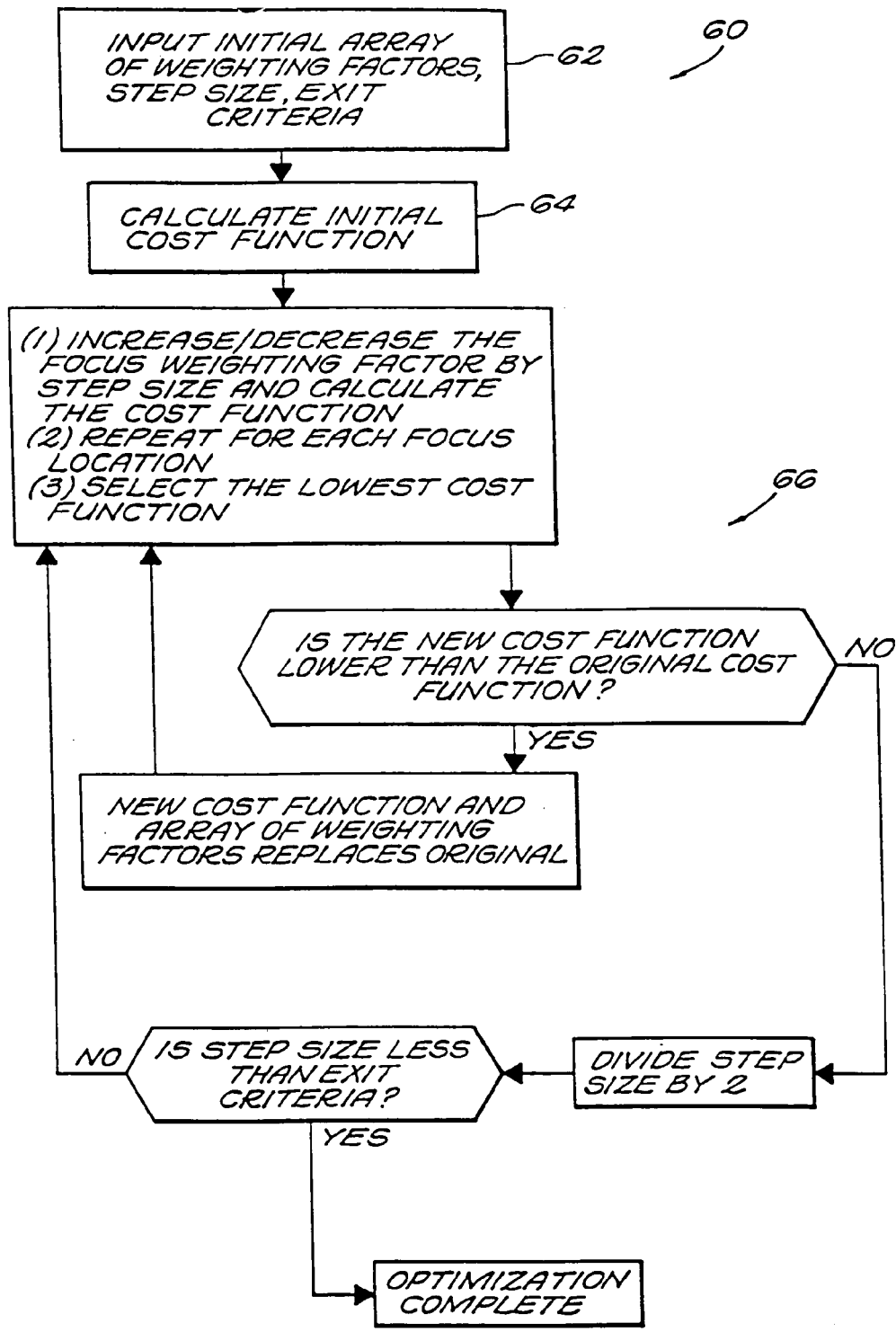
FIG. 4 is a block diagram of a deterministic method of optimizing focus weighing factors to achieve uniform temperature or dose profiles.

Another algorithm, to optimize the focus weighing factors to achieve uniform temperature or dose profiles, is a profile optimization algorithm which is shown in the block diagram of FIG. 4. The goal of the profile optimization algorithm is to select foci weighing factors that would produce uniform temperature and dose profiles in the body tissue at a desired scan location. The algorithm minimizes a cost function which is preferably designed to even out the temperature or dose along the width of the scan. FIG. 4 shows a block diagram of the algorithm for selecting foci weighing factors. The first step 40 involves imputing an initial array of weighing factors, step size and exit criteria. An initial cost function 42 is calculated from the initial array values. Such a cost function 42 is presented below. The remainder of the algorithm iteratively minimizes the cost function 42 for the desired scan location.

Figure 5:
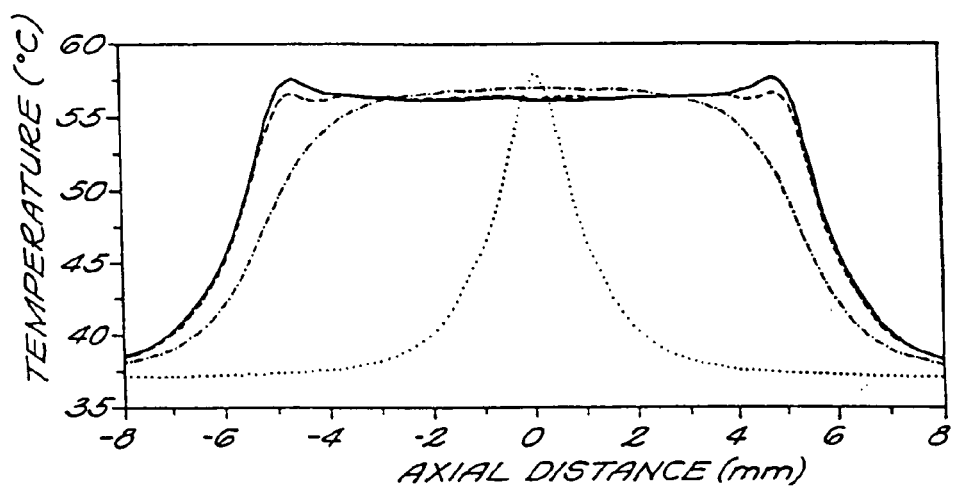
FIG. 5($a$) is a graphical representation of temperature simulations of a single stationary focus, a uniform power scan, a scan optimized for uniform temperature, and a scan optimized for uniform dose using the deterministic method of optimizing focus weighing factors of FIG. 4.
Figure 5:
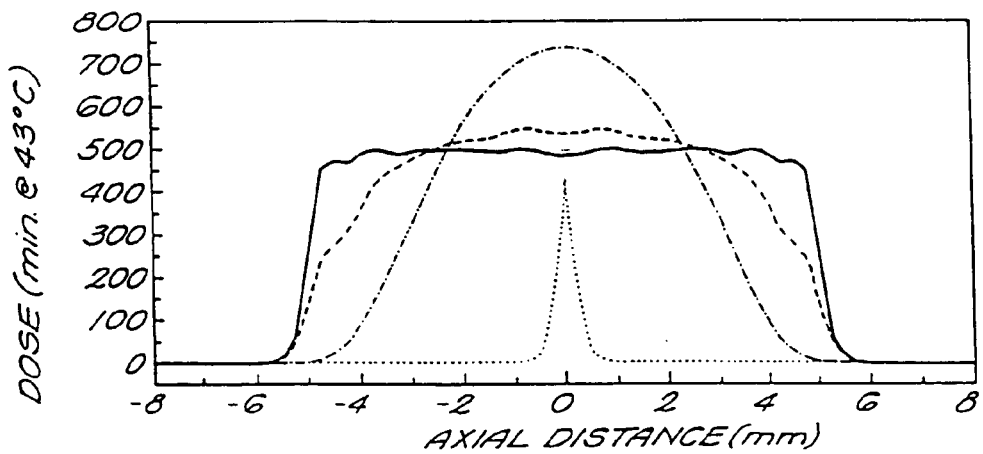
Figure 5:
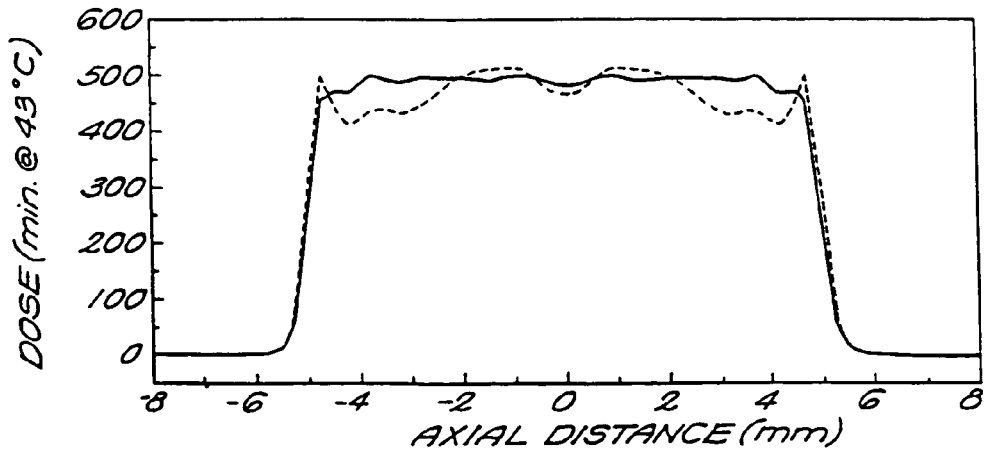

FIG. 5(a) shows simulations of body tissue temperature profiles at a focal depth of 3.5 cm for a single stationary focus, a uniform power scan, a scan optimized for uniform temperature, and a scan optimized for uniform dose. The body tissue temperature profile simulations of FIG. 5(a) use weighing factors derived with the profile optimization algorithm described in FIG. 4 and above. FIG. 5(b) shows dose profiles for the same simulation. FIG. 5(c) shows a smoother dose profile achieved when the optimization width is narrower than the scan width. The optimization width refers to the width over which the cost function is calculated. However, weight factors associated with foci outside of the optimization width, but within the scan width, can be adjusted during optimization. In comparison to the uniform power scan, all optimized scans produced less heating in the scan center and more heating near the scan endpoints, which resulted in a wider more evenly heated body tissue volume, especially for the dose optimized scan. It can be seen that electronic scanning is capable of significantly enlarging the thermally treated body tissue in comparison to a single stationary focus. A more detailed description of scanning and optimized scanning is provided below.

For ultrasound deposition in body tissue, high-frequency energy in the range of 0.1 to 100 MHz is desirable, though the aperiodic array design disclosed herein may be readily applied to arrays operating at other frequencies by appropriately scaling the element sizes based on the desired wavelength. An example of high-frequency ultrasound deposition and imaging is found in copending, commonly assigned application entitled "Methods and Apparatus for Image-Guided Ultrasound Delivery of Compounds Through the Blood Brain Barrier," filed Aug. 21, 1996, having Ser. No. 60/024,751, the teachings of which are incorporated herein by reference.

One of the most useful applications of the array, as described above, is in conjunction with magnetic resonance imaging (MRI) (not shown). Using a conventional MRI apparatus, temperature information and other characteristics within body tissue can be accurately determined. The MRI apparatus can be coupled to the controller 14 to provide interactive feedback. Thus, for example, with temperature information from the MRI apparatus, controller 14 can control ultrasonic energy deposition to precisely and concurrently treat diseased tissue, while minimizing harm to healthy tissue.

An Example of Element Arrangement and the Arrangement Optimization Algorithm

For an array consisting of randomly sized element with an infinite number of possible element widths within a given range, both the complexity of array construction and the amount of computation time required for simulation becomes limiting. To reduce array construction complexity and computation time, random distributions of two discrete element widths were studied. Limited simulations with three different element sizes suggest that combinations of three different element sizes may not yield better results than combinations of two different element sizes. However, it should be understood that more than two different element sizes may be used in alternative embodiments.

The goal of the optimization algorithm used in this example was to select distributions of two element widths in a linear planer arrangement which provided acceptable field patterns for a range of focal positions. The optimization technique used here involved the calculation of a cost function for different random distributions of two element widths. For each pair of element widths, a sufficient number of random distributions were simulated to evaluate the utility of the element pair, and the distribution with the lowest cost function was selected. In this evaluation, two hundred random element distributions were simulated to ensure that the selected distribution was within top 20% of all existing distributions and within 15% of the best achievable cost function for three focal positions. While the optimization algorithm used is this study provided meaningful results, other optimization methods may be used. Traditional methods such as gradient search techniques may not work very well since the selection of random element distributions is a discrete process that is certain to have a large number of local maxima and minima. Other procedures such as dynamic programming, which has been applied to sparse arrays in radar, or simulated annealing algorithms employ somewhat of a trial and error approach and may be appropriate.

The Cost Function

A cost function was used to quantitatively rank the acoustic power field for each array of uniform element width and each array consisting of random combinations of non-uniform element widths. The cost function, CF, for this example divided the maximum power in a grating lobe ($q_{lobe}$) by the maximum power at the focus ($q_{focus}$) for several different focus locations and then choosing the maximum, or worst case, since this will be limiting:

$$CF = \text{MAX}\left\{\frac{q_{lobe_1}}{q_{focus_1}}, \frac{q_{lobe_2}}{q_{focus_2}}, \frac{q_{lobe_3}}{q_{focus_3}}, \ldots, \frac{q_{lobe_n}}{q_{focus_n}}\right\} \quad (1)$$

where n=number of different focus positions. In other words, the cost function is a measure of the highest absorbed power in a grating lobe relative to the power absorbed at the focus. In comparing different random combinations of element widths, the cost function was calculated for three focus positions: a center focus and foci shifted 2 cm off axis, all at a 5 cm depth. Using three different foci was found to be sufficient to predict how well a specific random combination of element sizes would work for other focus positions. This was determined by simulating more focal positions for selected combinations of element widths. For example, the −2 cm to +2 cm range at 5 cm depth, is approximately the anatomically range over which a focus would be scanned to heat the prostate gland. Element sizes ranging from 0.7 mm (≈λ/2 center-center spacing) to 2.0 mm (≈1.4λ center-center spacing) in 0.1 mm increments were used in the simulations for both uniform and aperiodic arrays. As previously mentioned, the results presented in this study are only for arrays composed of uniform elements or random combinations of two different element sizes.

Figure 6:
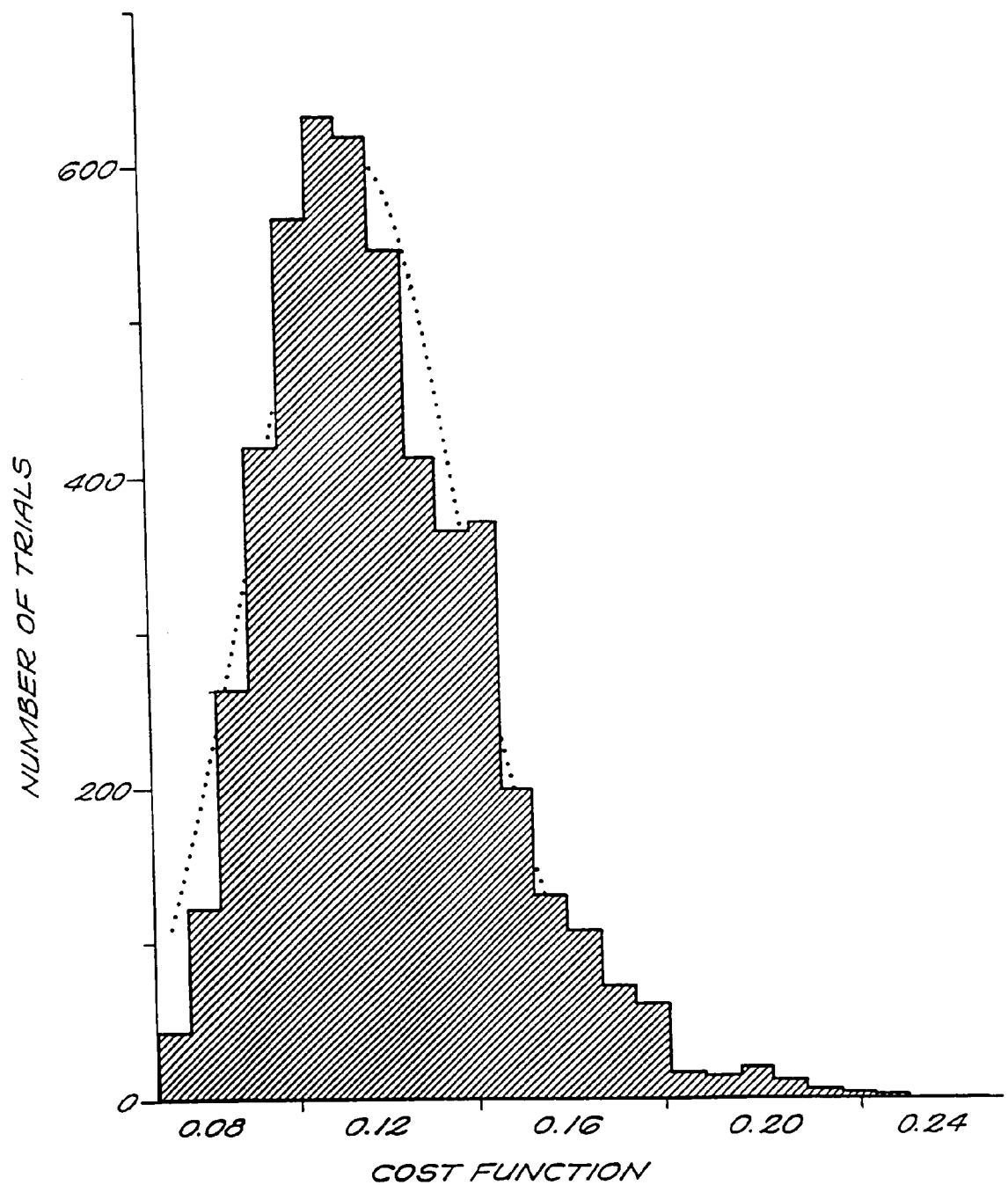
FIG. 6 is a cost function histogram for 5000 computer simulations of random arrangements of two radiating elements.

For comparing different random distributions of two element widths, 200 random distributions for each pair of element widths were simulated. Of the 200 trials for each pair of element widths, the distribution which produced the lowest cost function was considered an optimized random distribution and was used as a measure of the performance of that particular pair of element widths. Based on histograms for the sets of 200 trials and one 5000 trial histogram, the probability densities of these random element distributions were found to be approximately normal distributions. A normal curve was fit to the histogram for 5000 combinations of two element widths, as shown in FIG. 6. From this histogram and statistical theory of normal distributions, it was determined that selecting the best of the 200 trials would ensure selection of a distribution within the top 20% of all possible distributions with 99% confidence. Based on the 5000 trial distribution, it was determined with 98% confidence that the lowest cost function of the 200 trials would be within 15% of the lowest cost function achieved with the 5000 trials. With regard to the two confidence measures, the former ranks the selected distribution relative to other distributions, whereas the latter ranks the selected distributions cost function relative to the best cost function achievable. While this optimization strategy does not find the absolute best element distribution, it finds a distribution that is sufficiently close to the best to allow evaluation of the array parameters. Another imposed constraint was that equal numbers of each of the two element sizes be used. The effect of using different ratios of one element size to the other was also studied.

The cost function was based on acoustic power for two reasons. First, the computation time required to calculate 2-D power fields is approximately 100 times shorter than the time required to calculate 3-D power, steady state temperature and transient temperature fields, which would be needed for a temperature and/or thermal dose based cost function. The large difference in computation time becomes critical when it is considered that 200 cost functions were calculated for each combination of two element widths. Second, acoustic models allow for more direct array evaluation since thermal models introduce new physiological parameter uncertainties which, especially in hyperthermia, could mask array performance. While not included in the cost function optimization, the heating capabilities of this aperiodic array design, specifically the thermal surgery capabilities, were explored theoretically and experimentally in detail in a subsequent study.

Acoustic Simulations

The acoustic pressure field generated by a linear planer array of ultrasound planar transducers was simulated on a computer. The array 17 was modeled as a series of rectangular elements of equal length (15 mm) and specified widths, separated by 0.1 mm wide non-emitting spacers. The power amplitude and phase of each element were independently controllable and the phases were discretized to the nearest 22.5 degrees to match the resolution of the phase shifters. This phase shift resolution was sufficient for the purposes of this study. The acoustic pressure field was calculated using Huygen's principle, by modeling each element surface as a grid of simple hemispherical sources and then summing the contribution from each source to each point in the field. A grid spacing of was found to be sufficient to accurately model the rectangular elements. The magnitude of the pressure generated from each simple source was calculated using the complex surface velocity of the element which is based on the specified total acoustical output power from the array. The pressure at any field point in the tissue, $p_i(x,y,z)$, due to one simple source, was calculated using the following expression:

$$p_i(x, y, z) = \sqrt{\frac{2W\rho}{cA}} \left(\frac{fS}{D}\right) e^{\{(\phi - \frac{2\pi}{\lambda})i - d\alpha\}} \quad (2)$$

where W=total acoustical power output from the array, $\rho$=density (998 kg/m$^3$), c=the speed of sound (1500 m/s), A=total array surface area, f=frequency (1 MHz unless otherwise stated), S=area of each simple source, d=distance from the simple source to the field point, $\phi$=phase of the simple source, $\lambda$=wavelength, and $\alpha$=attenuation. For the optimization calculations, tissue was the simulated medium ($\alpha$=10 Np/m/MHz), but for comparisons with the ultrasound fields generated by the actual array and measured in water, water was the simulated medium ($\alpha$=0 in water). The pressure at any field point was calculated by summing the contributions from n simple sources:

$$P(x, y, z) = \sum_{i=1}^{n} p_i(x, y, z) \quad (3)$$

Then using the calculated pressure, the power deposition q(x,y,z) was calculated using the following expression:

$$q(x, y, z) = \frac{\alpha P^2(x, y, z)}{\rho c} \quad (4)$$

Array Simulations

Figure 7:
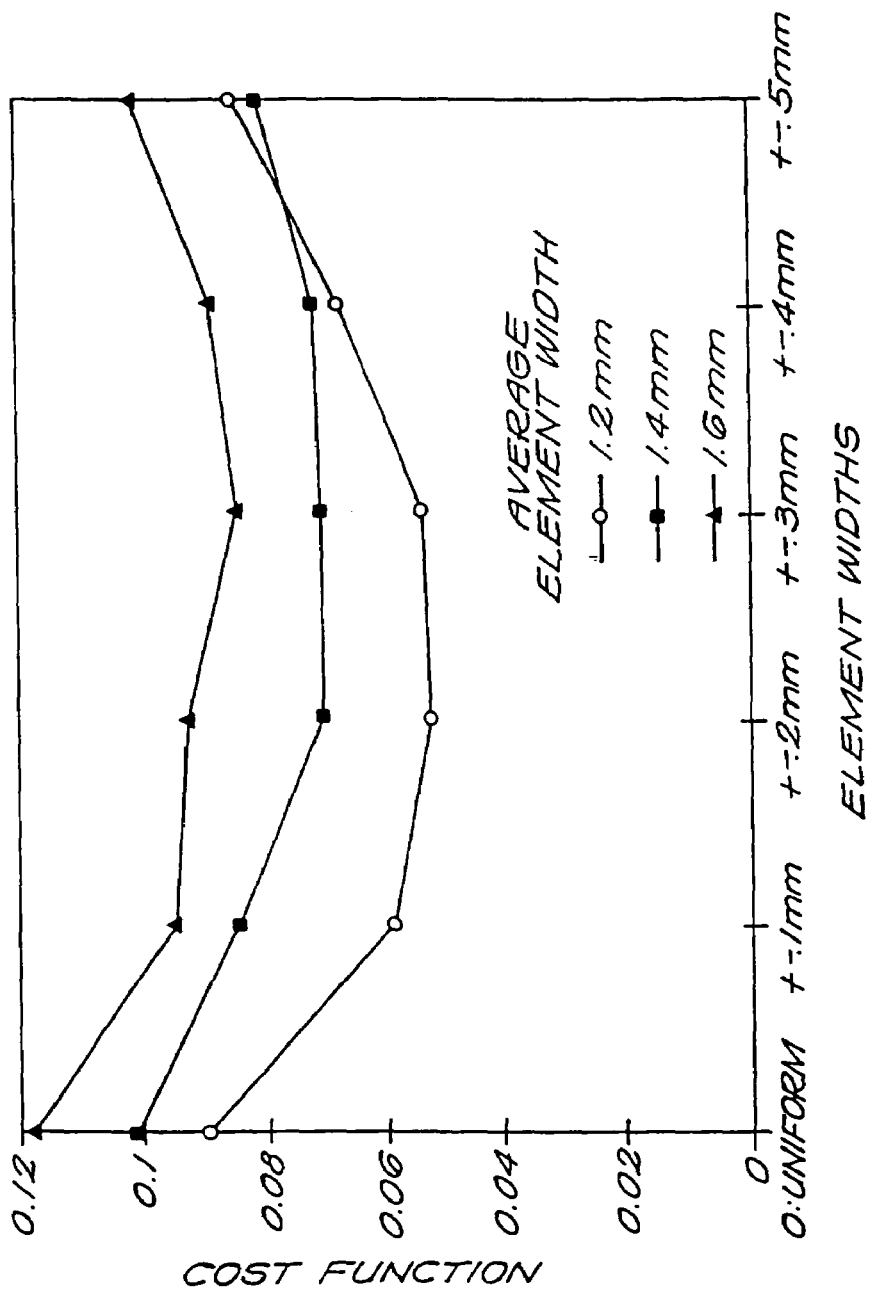
FIG. 7 is a graph of the effect of random distributions of two element widths on grating lobes for a constant average element width. Element widths are expressed in difference from the average element width at a frequency of 1 MHz and an array length of about 8.7 cm.
Figure 8:
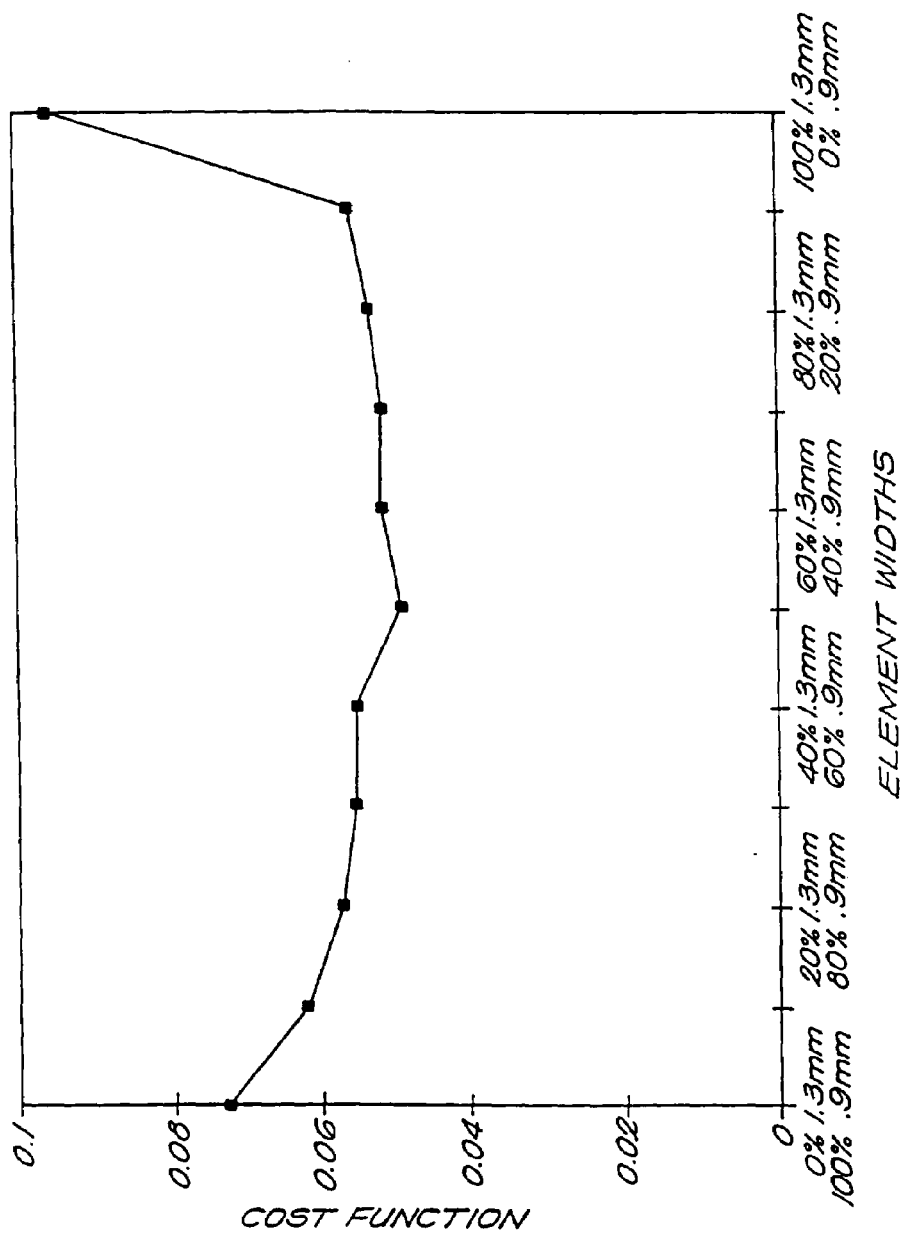
FIG. 8. is a graph of the effect of using different ratios of two unequal element widths on grating lobes with a frequency of 1 MHz and an array length of about 8.7 cm.

The results of the random element distribution optimization study are summarized in Tables 1 and 2 and FIGS. 7 and 8. The best random distributions of two element widths as determined by 200 trials with three focal positions per trial were compared to arrays of uniform elements. By comparing cost functions, it was discovered that aperiodic arrays allow for smaller grating lobes and/or larger element widths than uniform arrays. As shown in Table 1 for average element widths of 1.1 mm to 1.6 mm, the cost function was reduced by an average of 0.034 (or 34%) by using aperiodic arrays rather than uniform arrays. If the grating lobe levels are acceptable using uniform arrays, but larger elements are desired, it was found that aperiodic arrays could be used to increase the average element width by 0.34 mm (or 27% or $\lambda/4.4$) as shown in Table 2. FIG. 7 shows the ability of combinations of different element sizes to reduce the grating lobe level, while maintaining a constant average element width. There is a general trend that as the two element widths begin to deviate from their average width, the grating lobes first decrease and then begin to increase as the size difference between the two widths becomes larger.

TABLE 1

Grating lobe reduction for a constant average element width.
A comparison of cost functions for arrays with uniform element widths and aperiodic arrays with optimized random distributions of two element widths.

| Uniform Element Width | Cost | Random Element Sizes | Cost | ΔCost |
|---|---|---|---|---|
| 1.1 mm | .072 | 0.9 & 1.3 mm | .049 | −.023 (32%) |
| 1.2 mm | .090 | 1.0 & 1.4 mm | .053 | −.037 (41%) |
| 1.3 mm | .097 | 1.1 & 1.5 mm | .054 | −.043 (44%) |
| 1.4 mm | .101 | 1.2 & 1.6 mm | .071 | −.030 (30%) |

TABLE 1-continued

Grating lobe reduction for a constant average element width.
A comparison of cost functions for arrays with uniform element widths
and aperiodic arrays with optimized random distributions of two
element widths.

| Uniform Element Width | Cost | Random Element Sizes | Cost | ΔCost |
|---|---|---|---|---|
| 1.5 mm | .111 | 1.1 & 1.8 mm | .076 | −.035 (32%) |
| 1.6 mm | .118 | 1.3 & 1.9 mm | .081 | −.037 (31%) |

TABLE 2

Average element width increases for a constant grating lobe level
achieved by using aperiodic arrays with optimized random distributions
of two element widths instead of arrays with uniform element widths.

| Uniform Element Width | Cost | Random Element Sizes | Cost | ΔElement Width |
|---|---|---|---|---|
| 1.1 mm | .072 | 1.2 & 1.6 mm | .071 | +0.30 mm (27%) |
| 1.2 mm | .090 | 1.3 & 1.9 mm | .086 | +0.40 mm (33%) |
| 1.3 mm | .097 | 1.5 & 1.8 mm | .093 | +0.35 mm (27%) |
| 1.4 mm | .101 | 1.5 & 1.9 mm | .101 | +0.30 mm (21%) |

Until now, all of the aperiodic array results have been for arrays consisting of half of a first element size and half of a second element size, with the lowest cost function arising from a selected distribution of 50% 0.9 mm and 50% 1.3 mm elements. Ratios other than 50%/50% were investigated to determine if lower cost functions could be achieved. FIG. 8 shows costs functions for ratios ranging from 100% 0.9 mm and 0% 1.3 mm to 0% 0.9 mm and 100% 1.3 mm. The results shown in FIG. 8 indicate that a 50%/50% ratio provided the lowest cost function, although all ratios that included nonzero numbers of both element sizes produced lower cost functions than did uniform arrays consisting of either all 0.9 mm or all 1.3 mm elements. While a thorough simulation study was not conducted using combinations of three different element sizes, using 33% 0.9 mm, 33% 1.1 mm and 33% 1.3 mm elements corresponded to the same average element width as using 50% 0.9 mm elements and 50% 1.3 mm elements but lead to a cost function of 0.054 as opposed to 0.049.

Figure 9:
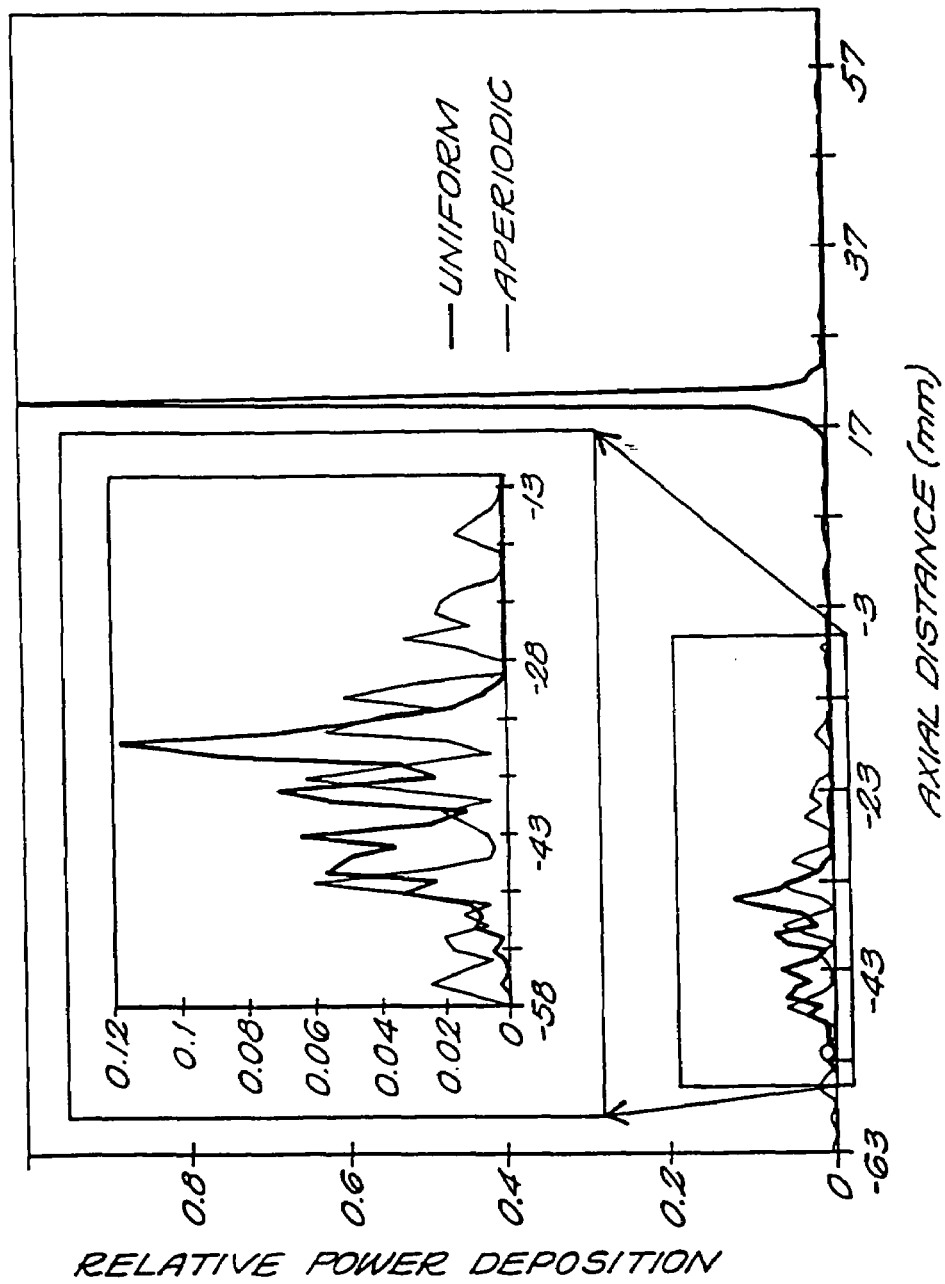
FIG. 9 is a graph of simulated power profiles for uniform arrays with a blow-up of the grating lobe region at a frequency of 1 MHz and a 5 cm deep focus shifted 2 cm off the center axis.

Comparisons of relative power profiles for a uniform (54 1.5 mm wide elements) and aperiodic array (27 1.1 mm wide and 27 1.9 mm wide elements) having the same average element width (1.5 mm) are shown in FIG. 9. The main beam for each array was virtually identical, however visible differences existed in the grating lobe regions. The peak grating lobe magnitude generated by the aperiodic array was only about half of the peak grating lobe magnitude generated by the uniform array, but the grating lobe width was larger for the aperiodic array than the uniform array.

Element Width Evaluation

As described above, a 50%/50% ratio provided a lower cost function than other ratios of 0.9 mm and 1.3 mm elements. An interesting finding was that all ratios consisting of both 0.9 mm and 1.3 mm elements produced lower cost functions than did uniform arrays consisting of either all 0.9 mm or all 1.3 mm elements. Of particular interest was the finding that replacing only 10% of the elements in a uniform 1.3 mm array with appropriately placed 0.9 mm elements could reduce the cost function from 0.097 to 0.057, a reduction of 41%. Even with this marked reduction in the cost function, an even greater reduction can be achieved (0.097 to 0.054) by using a 50%/50% combination of 1.1 & 1.5 mm elements, suggesting again that 50%/50% ratios of element widths will lead to the lowest cost functions. An additional point regarding this last comparison is that replacing 10% of the 1.3 mm elements with 0.9 mm elements will result in a average element width slightly less than the 1.3 mm average element width associated with an array composed of 50% 1.1 mm and 50% 1.5 mm elements.

The acoustical field scans were in good agreement with the theoretical simulations. A slight discrepancy was apparent for the comparison of the 5 cm deep focus shifted 2 cm off axis. In this case a small 10% grating lobe appeared in the simulation but not in the actual field measurement. This discrepancy may be explained by experimental uncertainty, and for example could have arisen from a slight directionality bias in measurements with the hydrophone. From the field measurements, the array demonstrated the ability to focus at depths up to 5 cm and 2 cm off axis with no 10% grating lobes present. Though the results were not included, the array was able to focus with at 5 cm deep and 3 cm off axis, but with small regions of 10% grating lobes. It is likely that grating lobes 10% or larger may not be a problem during hyperthermia, due to the smoothing effects of conduction and perfusion, especially when scanning a focus, which tends to spread out the effects of grating lobes; however, for thermal surgery, smaller grating lobes may become more significant, especially if regions of bone are near the target volume. For this reason, this aperiodic array design may show greater improvements over uniform arrays in thermal surgery applications, rather than hyperthermia applications. Given the anatomical location and size of the prostate, the ability of this array to scan a single focus is useful as a means of delivering power to the prostate and other internal body tissues.

Array Construction

Figure 10:
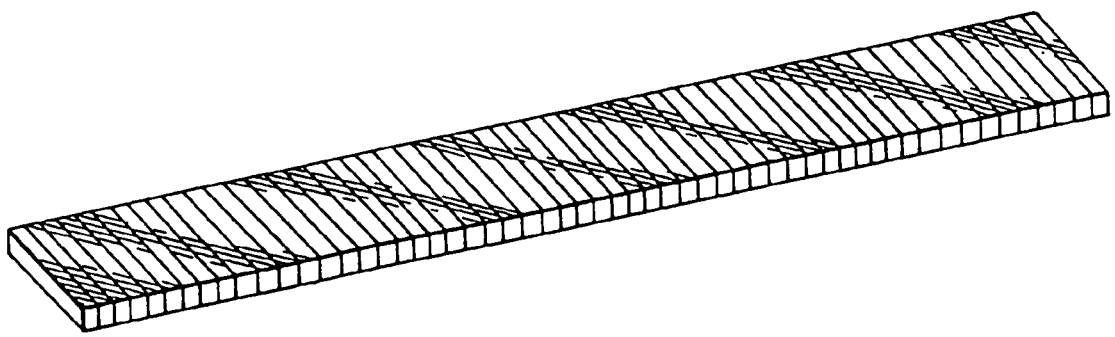
FIG. 10 is a schematic diagram of an experimental 57 element array according to the present invention.

As shown in FIG. 10, a 57 element linear planer array was constructed with 29 1.6 mm wide elements and 28 1.2 mm elements (87 mm total array length, 0.85λ average center-center spacing), using an optimized random distribution of two element widths based on the computer simulations. The elements were made from PZT-EC69 (EDO, Salt Lake City, Utah) material and operated in their thickness mode at a resonant frequency of 830 kHz. Silicone rubber adhesive of 0.13 mm thickness was used to glue the elements together and provide mechanical and electrical isolation. The array was then mounted in an acrylic frame. The elements were connected to RG-178 coaxial cable on the air-backed side using pogo pins. The elements on the front face of the array were grounded using silver epoxy and soldered to silver foil. Each element was electrically matched to 50-Ω load using L-C matching networks. Fifty seven channels were used of a 64 channel computer controlled amplifier system that consisted of phase shifters, duty cycle controllers, amplifiers, and RF power meters. A similar array of 16 elements was constructed to test the power capabilities of this material and this aperiodic array design technique. This array consisted of an optimized random distribution of 8 1.1 mm elements and 8 1.5 mm elements (26 mm total length), and was operated at 850 kHz.

Measurement of Element Efficiency and Power Output

Prior to array construction, the efficiency of elements cut to a range of different widths were measured using a radiation force technique. The element efficiency is the quotient of total acoustic output power divided by total electrical input power. The resonant frequency, originally 1.0 MHz, was measured for each of the element sizes, and each element was powered at its resonant frequency to achieve maximum element efficiency. The total acoustical power output of the 16 element array was measured for a 3 cm deep center focus.

Electrical Focusing and Phase Error Correction

Single and double foci were produced with the phased array by setting the phases of each element so that constructive interference of the pressure waves from each element occurred at the desired focal position(s). The required phase for each element was calculated using the differences in path length from the center of each element to the focus:

$$\phi_i = \frac{360°}{\lambda}(d_i - d_o) + 360°n \quad (5)$$

where $\phi_i$=phase of element i in degrees, $d_i$=distance from the center element i to the focus, $d_o$=reference distance (e.g. focus depth), n=an integer used to maintain $0 \leq \phi_i \leq 360°$. Two foci were generated by using half the array to focus at one location and the other half of the array to focus at a second location.

The array was not perfectly flat, and due to slight elevation variations between elements, a correction factor was needed to improve the sharpness of the focus. The array was placed in a tank of degassed, deionized water, and a needle-point (0.6 mm diameter) hydrophone (NTR, Seattle, Wash.) was used to measure the phases of each element individually so that pressure wave from each element would be in phase at the location of the hydrophone. Using the phases measured with the hydrophone and those calculated with (5), an elevation error was calculated for each element. Using the elevation error for each element, $\epsilon_i$, a corrected equation was used to calculate the phases for any focal position:

The phase corrections were based on the error between the calculated-uncorrected and hydrophone measured phases for a 4 cm deep center focus. To verify the validity of the phase $$\phi_i = \frac{360°}{\lambda}(d_i - d_o + \epsilon_i) + 360°n \quad (6)$$

corrections, ultrasound fields generated using corrected phases were compared to fields generated by hydrophone measured phases for other focal positions.

Ultrasound Field Measurements

The array was placed in a tank of degassed, deionized water, and the ultrasound field was measured by mechanically scanning a hydrophone. The grid spacing for the measurements varied from 0.25 mm to 1 mm, depending on the scan. Prior to scanning a full 2-D field, 1-D scans were performed to gauge the required field length and width so as not exclude significant portions of the field near the edges (i.e. grating lobes).

Material Characteristics

Figure 11:
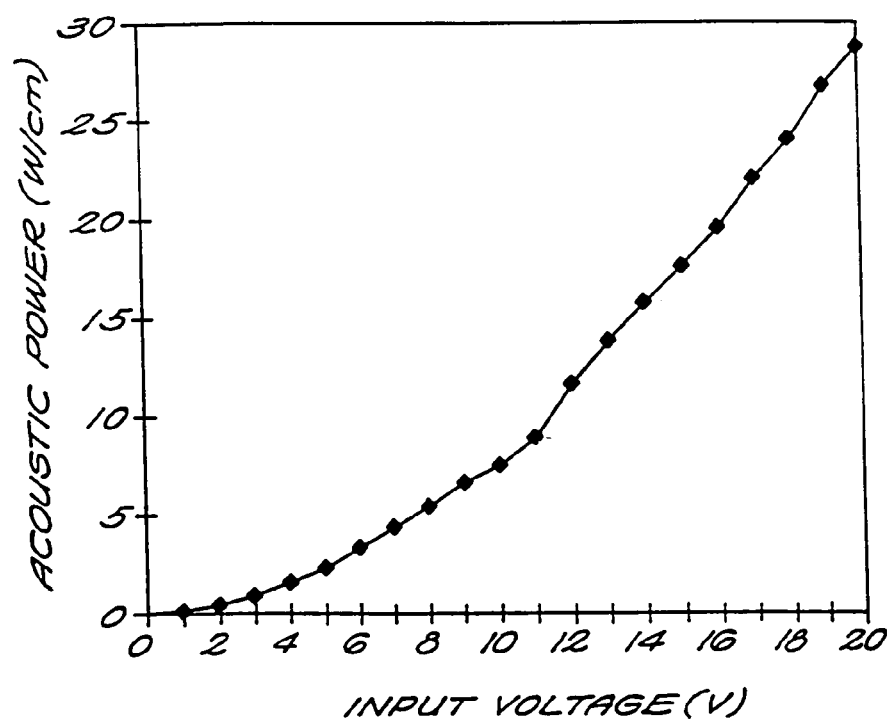
FIG. 11 is a graph of experimental data showing acoustical power output per cm of array length (W/cm) measured in water from a 16 element aperiodic array according to the present invention having a frequency of 0.85 MHz, a 3 cm deep center focus, and an array length of approximately 2.7 cm.

As shown in Table 3 the efficiency of the elements tended to decrease as the element width decreased with the exception of the 2 mm element width. FIG. 11 shows the power capabilities of using PZT-EC69 in an aperiodic array design. The power measurements were performed with a 16 element array, prior to construction of the 57 element array to determine if sufficient acoustical power output was attainable. The array was able to generate 28 W of acoustical power per cm of array length while focusing at 3 cm deep. The power limitations of this array were never realized as it performed robustly for the duration of the power measurements without any noticeable losses in efficiency or damage to the array.

TABLE 3

PZT -EC69 material properties for different element widths.
Original frequency prior to cutting material: 1.05 MHz.

| Element Width | Efficiency | Resonance |
| --- | --- | --- |
| 1.0 mm | 38% | .89 MHz |
| 1.5 mm | 46% | .82 MHz |
| 2.0 mm | 29% | .91 MHz |
| 5.0 mm | 62% | 1.02 MHz |
| 15.0 mm | 83% | 1.05 MHz |

Phase Corrections

Figure 12:
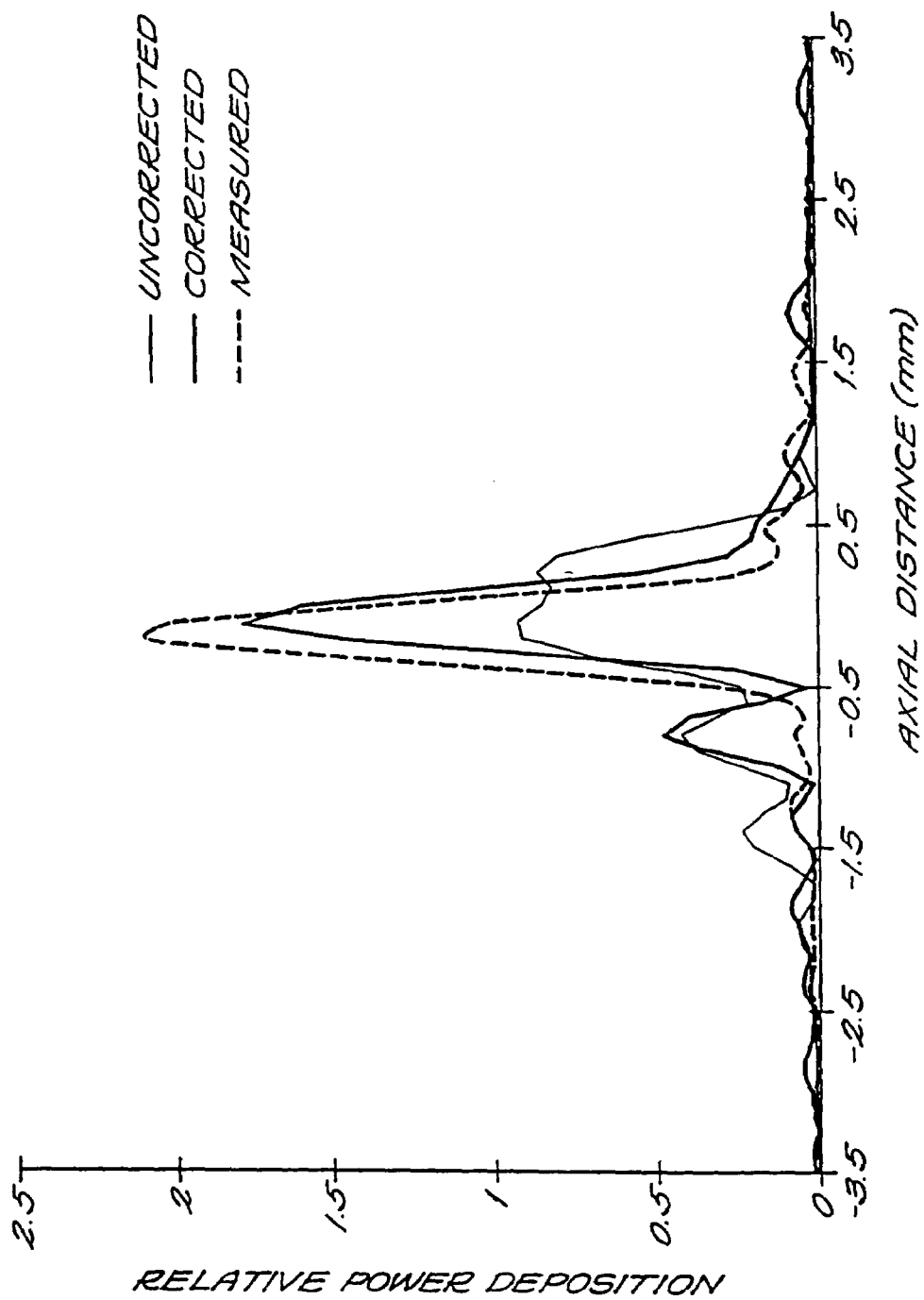
FIG. 12 is a graphical comparison of axial power profiles generated by calculated-uncorrected, calculated-corrected, and hydrophone measured phases for the 57 element aperiodic phased array of FIG. 9 with a frequency of 0.83 MHz and a 3 cm deep focus shifted 2 cm off the center axis.
Figure 13A:
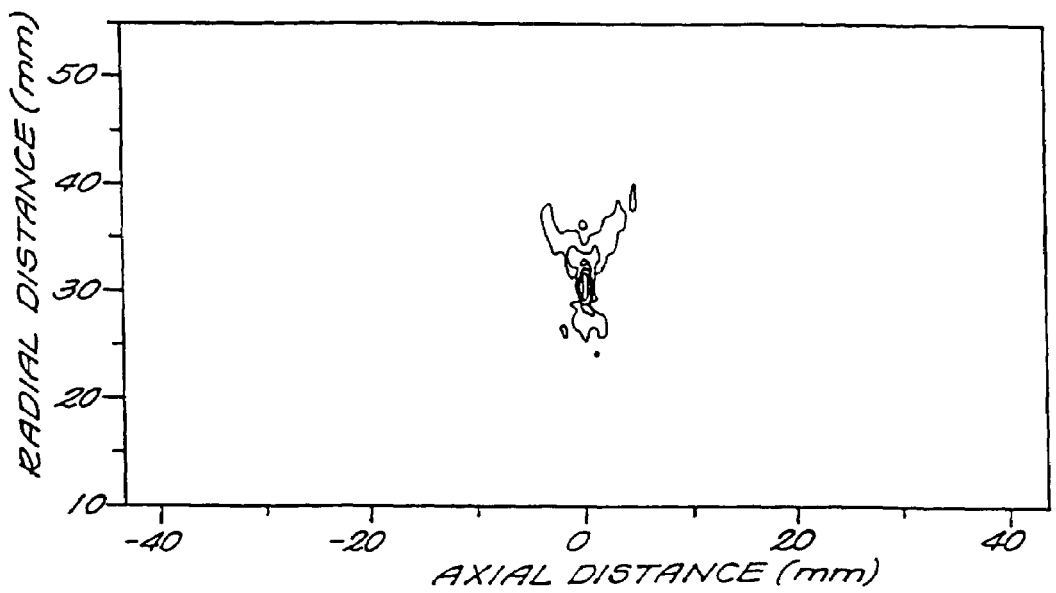
FIG. 13($a$) is a graph of a measured ultrasound field from the 57 element aperiodic phased array of FIG. 9 in a graphical format with an array frequency of 0.83 MHz and a 3 cm deep center focus.
Figure 13B:
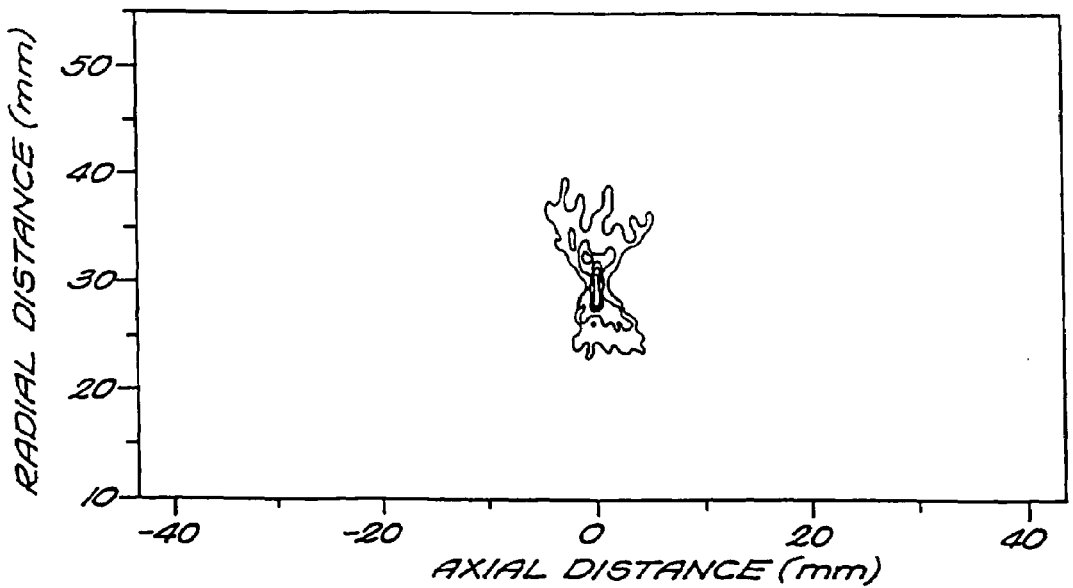

The 57 element array was able to focus at different specified locations using the uncorrected calculated phases given by equation (5). The corrected phases given by equation (6) generated a sharper focus than that produced by the uncorrected phases. The best focus however was produced by phases measured with a hydrophone. FIG. 12 shows a comparison of power profiles generated by uncorrected, corrected and measured phases for a 3 cm deep focus shifted 2 cm off axis.

Comparison of Field Measurements and Simulations

Figure 14:
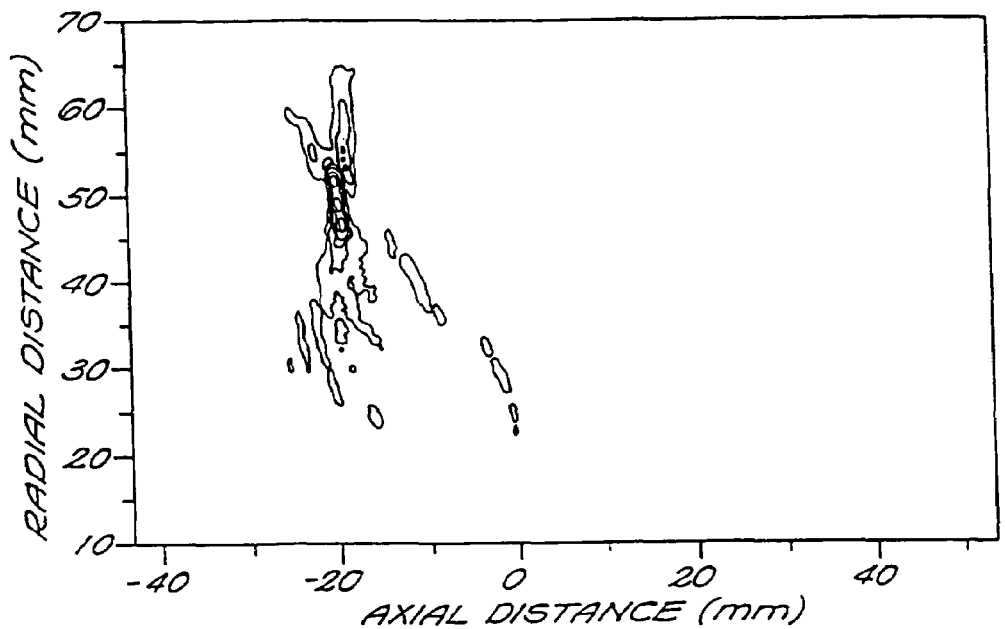
FIG. 14($a$) is a graph of a measured ultrasound field from the 57 element aperiodic phased array of FIG. 9 in a graphical format with an array frequency of 0.83 MHz and a 5 cm deep center focus shifted 2 cm off the center axis.
Figure 14:
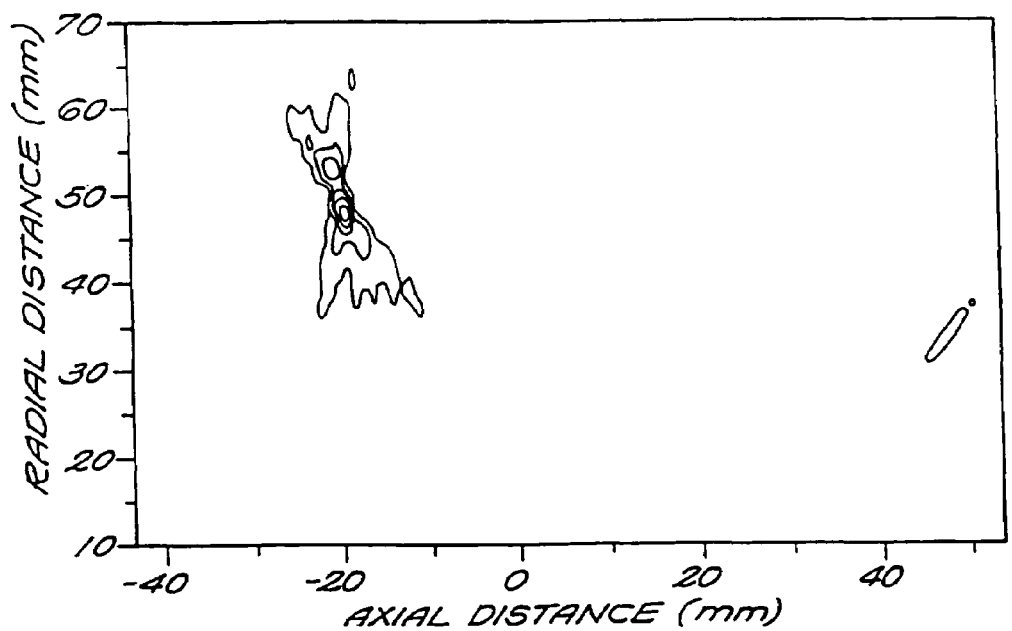
Figure 15A:
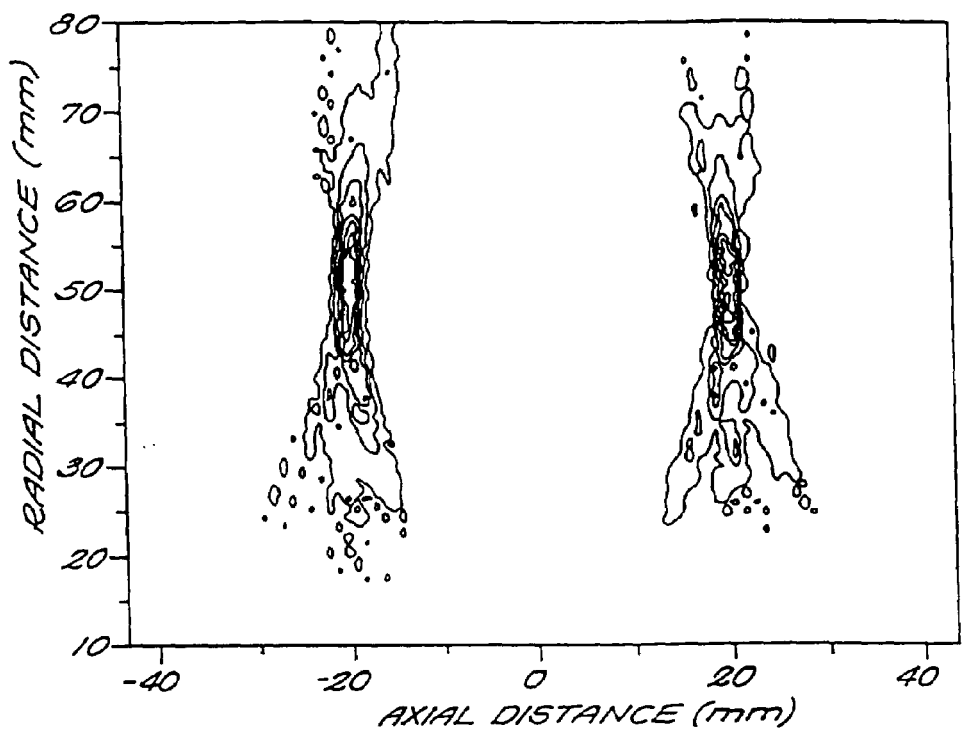
FIG. 15($a$) is a graph of a measured ultrasound field from the 57 element aperiodic phased array of FIG. 9 in a graphical format with an array frequency of 0.83 MHz and two 5 cm deep foci 2 cm off the center axis.
Figure 15B:
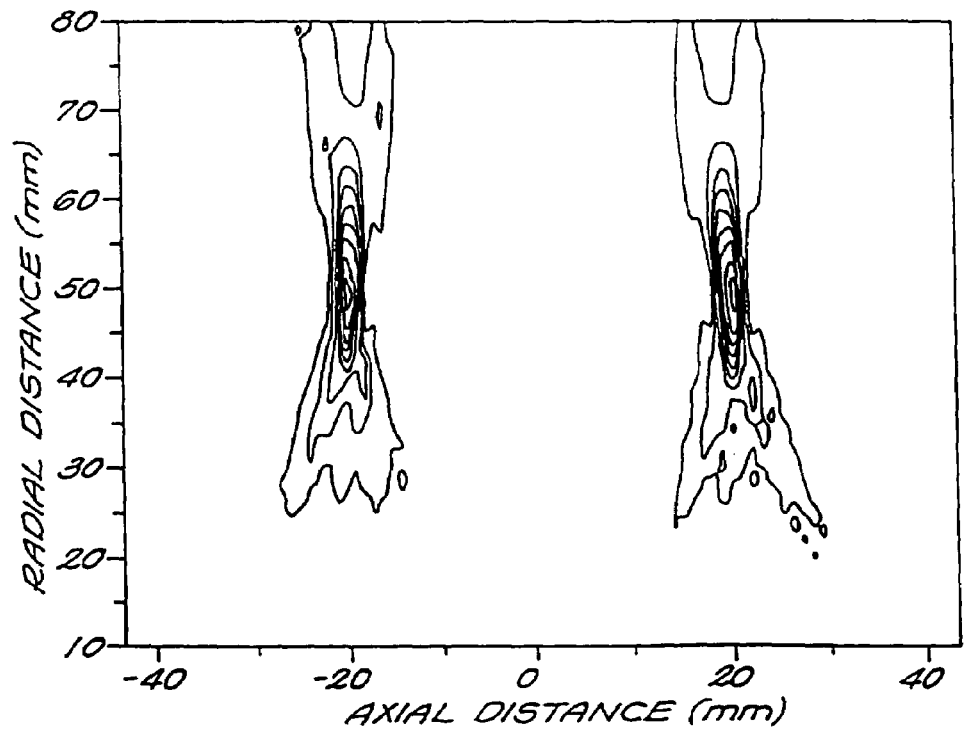
Figure 16:
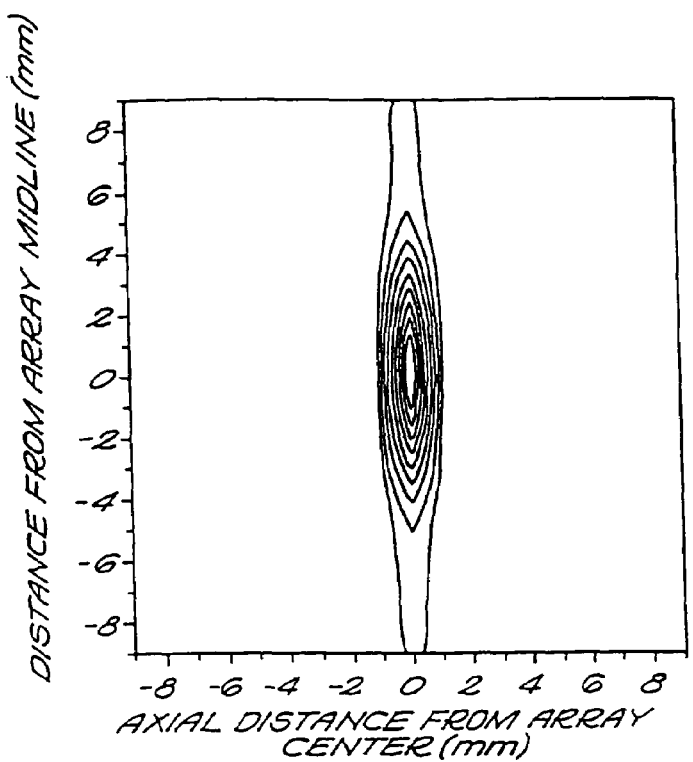
FIG. 16($a$) is a graph of a measured ultrasound field from the 57 element aperiodic phased array of FIG. 9 in a graphical format with an array frequency of 0.83 MHz and a 5 cm deep center focus.
Figure 16:
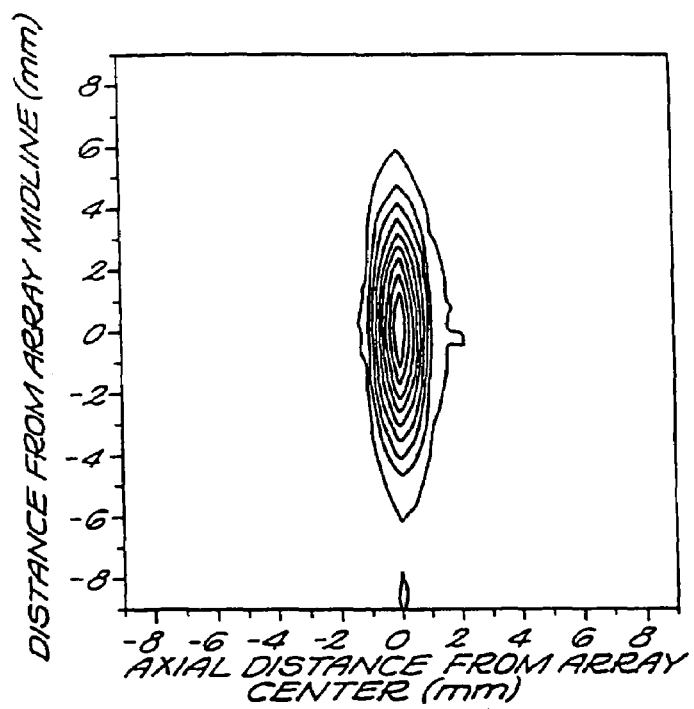

The 57 element aperiodic array was able to produce a single focus at the following focal positions while keeping the grating lobe peak intensity below 10% of the focus intensity: 3 cm deep center (FIG. 13), 4 cm deep center (not shown) to 2 cm off axis (not shown), and 5 cm deep center (not shown) to 2 cm off axis (FIG. 14). The 4 cm deep focus, shifted 2 cm off axis corresponds to a steering angle of 26.5° with all grating lobes less than 10%. Grating lobes greater than 10% were present for foci at the following locations: 3 cm deep 2 cm off axis, and 5 cm deep 2.5 and 3 cm off axis (not shown). Double foci were produced at 5 cm deep, each 2 cm off axis, by splitting the array in half and using each half to produce its own focus (FIG. 15). The focus width and length in plane parallel to the array was measured to be 5 mm×2 mm at a 5 cm center focus for a 50% beam contour (FIG. 16). As a means of validating the model, measured ultrasound power field were compared to those simulated and were in close agreement for all focal positions tested as shown in FIGS. 13–16. Both the simulated and the measured ultrasound fields are shown with 10% contour levels of the normalized peak power.

An Example of Scanning and Optimization of Focus Weighing Factors

An advantage that phased arrays have over geometrically focused transducers is that they are able to electronically scan a single focus over a specified range very quickly. Study has demonstrated that the necrosed tissue volume may be increased by more than a factor of 300 by using electronic scanning. The ability of linear ultrasound phased arrays to create necrosed tissue lesions was demonstrated experimentally in fresh beef liver using a single stationary focus and single focus scans generated by an aperiodic 0.83 MHz, 57 element linear ultrasound phased array.

Also investigated was the ability of phased arrays to increase the necrosed tissue volume by uniform and optimized electronic scanning of a single focus. Previous studies have investigated optimized temperature distributions for hyperthermia treatments, but prior to this study optimization of necrosed tissue volumes has not been studied.

Optimization of Single Focus Scanning

It was determined that unequal weighing of different focal locations, in particular weighing the end scan points more, would result in a more uniform temperature and dose profile than that achieved by uniform weighing of each focus location. Due to the close foci spacing (0.5 mm), the system was not decoupled (i.e. changing the weighing factor of one focus affected the power at neighboring focal locations). For this reason, individually scaling the power at each point to produce a desired temperature was not possible, and an optimization technique was needed.

A simple direct search optimization algorithm was used to find foci weighing factors that would produce uniform temperature and dose profiles at the scan depth. The algorithm is outlined in FIG. 4. Symmetry was used since the scan was chosen to be symmetric about the central axis. For example, for a scan from −5 mm to +5 mm with 0.5 mm foci spacing, there are 21 focal locations but only 11 independent weighing factors exist, each of which may be incremented or decremented yielding a total of 22 possible directions. The cost function (CF) that was used is given in the following expression:

$$CF = \sum_{j=1}^{m} (X_j - X_{ave})^4 \quad (7)$$

where m is the number of field points along the width of the scan, $X_j$ is the temperature (or dose) at position j of the scan, and $X_{ave}$ is the average temperature (or dose) over the width of the scan.

This optimization algorithm can be used to achieve both uniform temperature and dose profiles. The advantage of optimizing temperature is that it requires much less computation time. For example, using temperature in the cost function requires calculating the temperature only during the sonication (5 seconds), but using dose in the cost function requires temperature and dose calculations during both the sonication and cool down period (often >70 sec). Although uniform temperature profiles do improve dose uniformity, they do not ensure that the dose profile is as uniform as possible. For this reason, the temperature was first quickly optimized, and then the result was used as a starting point for more computationally intensive dose optimization.

Experimentally Generated Necrosed Tissue Lesions

A 57 element array as described above was used to create necrosed tissue lesions in fresh beef liver. The array was 87 mm long, 15 mm wide and was operated at its resonant frequency of 0.83 MHz. The array was constructed using an optimized random distribution of two selected element widths, which was determined in a previous study to reduce grating lobe levels by approximately one-third relative to a uniform array with the same average element width. Prior to in vitro testing of the experimental array, the ability of this array to create necrosed tissue lesions was investigated using simulations. These simulations used the actual element widths, inter-element non-emitting spacers and phase discretization to more accurately model the parameters of the actual array and amplifier system.

The ability of the aperiodic phased array to create lesions in fresh beef liver was tested with a single stationary focus and uniform scans using a range of power levels and sonication times. The array and the liver were submerged in a tank of degassed water to reduce the effects of ultrasound reflections at gas-water interfaces. The water temperature was 23° C. and separated the array and liver surfaces by 1.5 cm, which is a reasonably approximation of the water bolus used for transrectal ultrasound treatments. The water temperature was set to 23° C. rather than 37° C. to provide a conservative estimate of the array's ability to generate necrosed tissue lesions.

Experimental Results

Figure 17A:
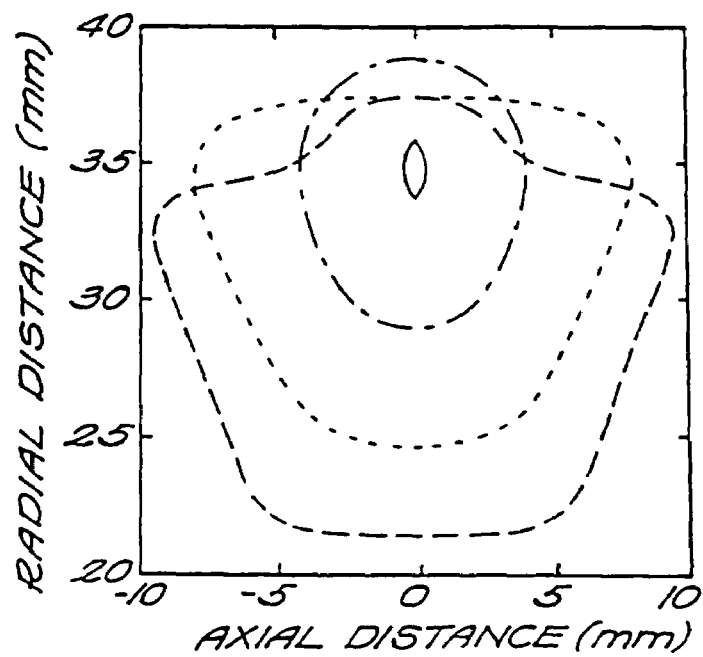
FIG. 17($a$) is a graph showing isothermal dose lines in a plane perpendicular to the array surface and parallel to the array length. The dose lines are for a single focus (solid line) and uniform power scans of 1 cm (dashed-dotted line), 2 cm (dotted line) and 3 cm (dashed line) axial widths produced by a 1 MHz 9 cm long array for 5 second sonications, maximum temperature=60° C. and perfusion=5 kg/(m$^3$s).
Figure 17B:
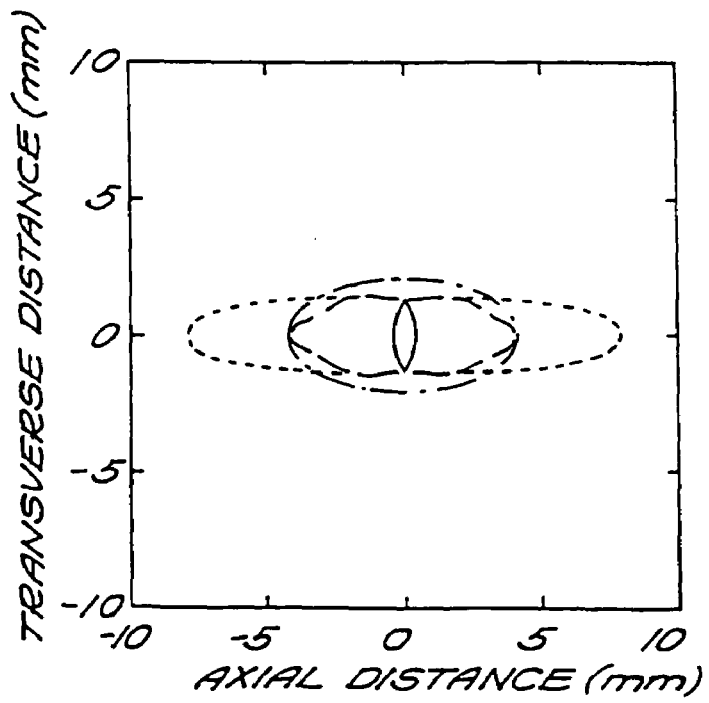

In FIGS. 17(a) and (b), the size of the necrosed tissue generated by a single focus is compared to those generated by electronic scans of varying width (i.e. a single focus was electronically scanned across 1, 2 and 3 cm axial widths at a constant radial depth of 3.5 cm). FIG. 17 shows isothermal dose lines (240 minutes at 43° C.) for a single focus (solid line) and uniform power scans of 1 cm (dashed-dotted line), 2 cm (dotted line) and 3 cm (dashed line) axial widths produced by a 1 MHz 9 cm long array for 5 second sonications, maximum temperature=60° C. and perfusion=5 kg/(m³s). FIG. 17(a) shows a plane perpendicular to the array surface and parallel to the array length. FIG. 17(b) shows a plane parallel to the array surface and 3.5 cm deep.

Optimized Electronic Scan Simulations

FIG. 5(a) shows the temperature and FIG. 5(b) the dose profiles at the focal depth (3.5 cm) for a single stationary focus, a uniform power scan, a scan optimized for uniform temperature and a scan optimized for uniform dose. The width of all scans was 1 cm (−5 mm to +5 mm). The uniform temperature scan was optimized from −5 mm to +5 mm (a), (b), and the uniform dose scan was optimized from −4.5 mm to +4.5 mm (a), (b), (c) and from −5 mm to +5 mm (c). FIG. 5(c) demonstrates that a smoother dose profile is achieved when the optimization width is narrower than the scan width. The optimization width refers to the width over which the cost function is calculated; however, weighing factors associated with foci outside of the optimization width but within the scan width can be adjusted during optimization. In comparison to the uniform power scan, all optimized scans produced less heating in the scan center and more heating near the scan endpoints, which resulted in a wider more evenly heated necrosed tissue volume, especially for the dose optimized scan. Again it can be seen that electronic scanning is capable of significantly enlarging the necrosed tissue volume in comparison to a single stationary focus.

Simulations for the Experimental Array

Figure 18:
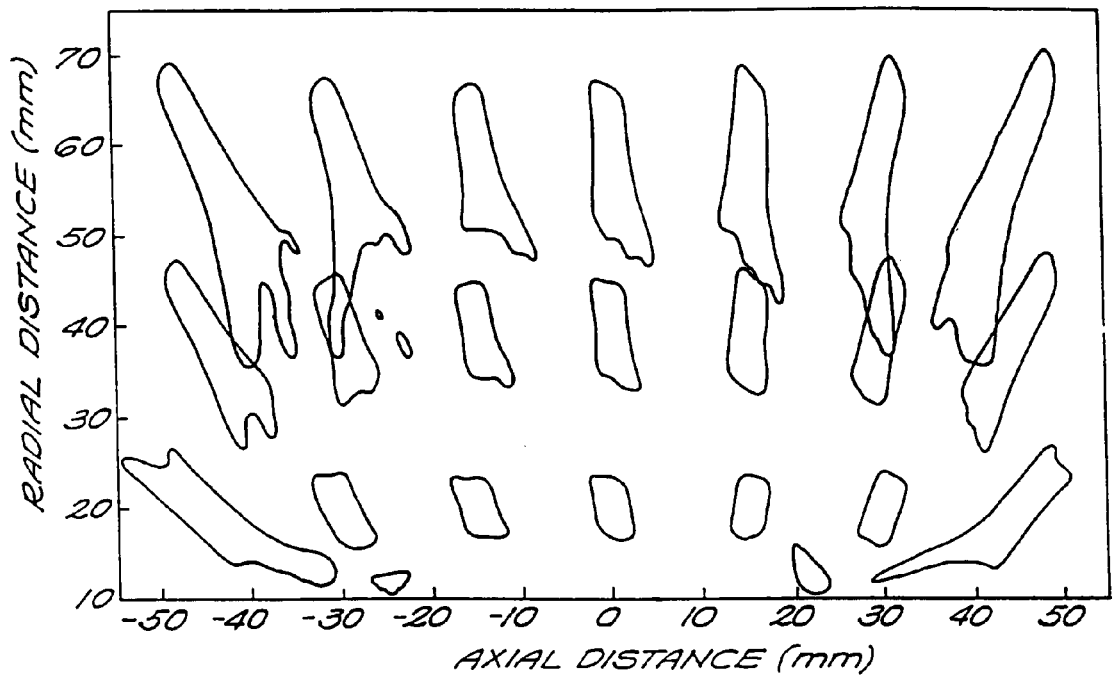
FIG. 18($a$) is a graph showing simulated necrosed tissue lesions in a plane perpendicular to the array surface and parallel to the array length.
Figure 18:
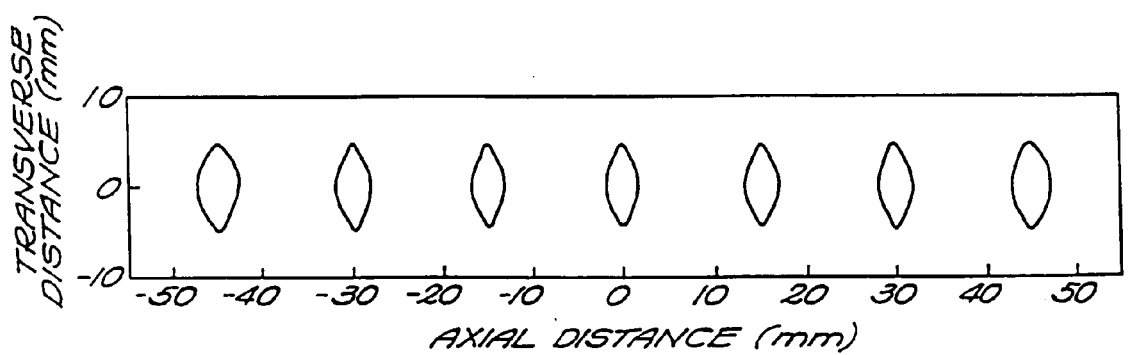

Simulated necrosed tissue lesions for the 0.83 MHz, 8.7 cm long, 57 element array of the type discussed above used in the in vitro experiments are shown superimposed in FIGS. 18(a) and (b). These predicted lesions are for 5 second sonications, maximum temperature= 100° C., and perfusion=5 kg/(m³s) for single foci at 2, 4, and 6 cm deep and 0.0, ±1.5, ±3.0, and ±4.5 cm off the central axis. Significant secondary lesions are present for the 2 cm deep ±4.5 cm off axis foci, and the necrosed tissue volume is discontinuous for the 6 cm deep −4.5 cm off axis focus.

In Vitro Experimental Necroses

The experimental array (in accordance with the invention as described above) was able to produce necrosed tissue lesions in fresh beef liver using both uniform scans and single stationary foci at different locations for sonication times ranging from 10 to 30 seconds. The lesion sizes listed in Table 4 represent approximate cross-sectional areas that were calculated using the product of the measured lesion width and length. Since the actual array acoustic power output could not be measured during the experiments, approximate acoustic power levels listed in Table 4 were estimated based on earlier acoustic power measurements.

Table 4. Beef liver lesions generated by 0.83 MHz, 8.7 cm long 57 element aperiodic linear phased array. All single foci were located on the central axis and 4 cm deep. The scan was symmetric about the central axis, 8 mm wide and 4 cm deep.

TABLE 4

Beef liver lesions generated by 0.83 MHz, 8.7 cm long 57 element aperiodic linear phased array. All single foci were located on the central axis and 4 cm deep. The scan was symmetric about the central axis, 8 mm wide and 4 cm deep.

| Sonication Time (s) | Estimated Acoustic Power (W) | Focus | Approximate Lesion Size (mm$^2$) |
|---|---|---|---|
| 10 | 140 | single | 8 |
| 20 | 140 | single | 32 |
| 20 | 140 | scan | 64 |
| 20 | 110 | single | 21 |

Of the methods studied for enlarging the necrosed tissue volume, electronic scanning of a single focus was demonstrated to be the most effective. Relative to a single focus sonication, scan widths of 1 and 2 cm increased the calculated necrosed tissue volumes by factors of 100 and 300 respectively, while holding the maximum temperature and sonication time constant.

While uniform scanning offered significant advantages over single stationary focus sonications, further improvement was realized with optimized scanning. For uniform scans, the center of the necrosed tissue volume received a dose much higher than the dose received near the volume boundaries. This overheating of the center and under heating of the target volume edges was minimized by optimally setting the weighing parameter associated with each focus location along the width of the scan. For a scan optimized to produce a uniform dose profile at the focal depth, the corresponding temperature profile was characterized by higher temperatures near the scan endpoints, and the corresponding pressure profile was even more uneven, with the pressure being much higher near the scan endpoints. Additionally, using a scan width one focal spacing wider than the optimization width resulted a smoother dose profile for the following reasons. When the entire width of the scan was optimized, a very steep gradient was needed at the scan endpoints to bring these points up to the desired dose. While increasing the power at the scan endpoints brought the endpoint doses up to the desired level, the points adjacent to the endpoints and towards the scan center received a higher dose due to conduction effects from the scan center. The dose at these adjacent points cannot be brought down to the desired level even when the power is decreased to zero at these points. Therefore, a more uniform dose can only be achieved by increasing the scan width relative to the optimization width. Another method of enlarging the necrosed tissue volume, which was not investigated in this study, is the generation of multiple foci simultaneously which can be stationary or electronically scanned to control the necrosed tissue volume. An additional area for further investigation is temperature build up in the near field during multiple scan sonications, which is an important consideration in determining the required cooling time between sonications and the total treatment time.

The ability of phased arrays to significantly enlarge the necrosed tissue volume by electronic scanning was established, as was the ability to produce more uniform temperature and dose distributions by optimizing scan weighing factors. The heating capabilities of linear phased arrays were verified experimentally by creating necrosed tissue lesions in beef liver, as listed in Table 4.

While there have been described herein what are considered to be preferred embodiments of the present invention, other modifications of the invention will be apparent to those skilled in the art from the teaching herein. Thus, for instance, whereas the examples above primarily concerned application of ultrasound energy doses for purposes of tissue ablation, it will be appreciated that the invention is equally applicable to providing doses for diagnostic imaging, drug delivery, and other therapies which employ heat, cavitation, shock waves or other thermal and/or mechanical effects for therapeutic purposes. t is therefore desired to be secured in the appended claims all such modifications as fall within the true spirit and scope of the invention. Accordingly, what is desired to be secured by Letters Patent of the United States is the invention as defined and differentiated in the following claims:

What is claimed is:

1. A method for depositing ultrasound energy in body tissue, the method comprising:
   emitting ultrasound energy from a first aperture and a second aperture with a center of the first aperture being displaced a first distance from a center of the second aperture; and
   emitting ultrasound energy from a third aperture having a center displaced a second distance from the center of the second aperture;
   wherein the second distance is different than the first distance and the third aperture has a size that is different than at least one of a size of the first aperture and a size of the second aperture;
   wherein the ultrasound energy is emitted from the apertures to produce a reduced grating-lobe beam of ultrasound energy in the body tissue;
   wherein the energy emitted from at least two of the first, second, and third apertures are produced in response to separate excitation signals; and
   wherein the second aperture is disposed adjacent the first aperture and the third aperture is disposed adjacent to the second aperture with the second aperture disposed between the first and third apertures.

2. The method of claim 1 further comprising independently controlling phases of the ultrasound energy emitted from the first, second, and third apertures.

3. The method of claim 2 wherein the phases are controlled to steer the beam through an angle up to approximately ninety degrees relative to a mainbeam direction of the emitted energy from the first, second, and third apertures with the phases of the emitted energy being the same.

4. The method of claim 2 wherein the phases are controlled to steer the beam to at least two distinct focal positions within the body tissue.

5. The method of claim 1 further comprising independently controlling amplitudes of the ultrasound energy emitted from the first, second, and third apertures.

6. The method of claim 1 further comprising independently controlling frequencies of the ultrasound energy emitted from the first, second, and third apertures.

7. The method of claim 1 further comprising independently controlling phases, amplitudes, and frequencies of the ultrasound energy emitted from the first, second, and third apertures.

8. The method of claim 7 wherein the phases, amplitudes, and frequencies are controlled such that the beam provides a substantially uniform temperature profile within a region of the body tissue.

9. The method of claim 7 further comprising imaging the body tissue and controlling the phases, amplitudes, and frequencies in response to the imaging.

10. The method of claim 9 wherein the imaging is magnetic resonance imaging.

11. The method of claim 1 wherein the emitting emits ultrasound energy from the apertures with frequencies between about 0.1 MHz and about 100 MHz.

12. The method of claim 1 wherein the separate excitation signals cause the energies emitted from the at least two of the first, second, and third apertures to have different phases.

13. A method for depositing ultrasound energy in body tissue, the method comprising:
    emitting ultrasound energy from a first plurality of apertures of a first size;
    emitting ultrasound energy from a second plurality of apertures of a second size different from the first size, the first and second apertures disposed in an array such that centers of the apertures are displaced from each other by at least two different distances; and
    independently controlling at least one of phases, amplitudes, and frequencies of the ultrasound energy emitted from the first and second pluralities of apertures;
    wherein the ultrasound energy is emitted from the apertures to produce a reduced grating-lobe beam of ultrasound energy in the body tissue; and
    wherein the at least two different distances are measured from one aperture to two adjacent apertures on opposite sides of the one aperture.

14. The method of claim 13 wherein the phases are controlled to steer the beam through an angle up to approximately ninety degrees relative to a mainbeam direction of the emitted energy from the first and second pluralities of apertures with the phases of the emitted energy being the same.

15. The method of claim 13 wherein the phases are controlled to steer the beam to at least two distinct focal positions within the body tissue.

16. The method of claim 13 wherein the phases, amplitudes, and frequencies are controlled such that the beam provides a substantially uniform temperature profile within a region of the body tissue.

17. The method of claim 13 further comprising imaging the body tissue and controlling the phases, amplitudes, and frequencies in response to the imaging.

* * * * *